US008323903B2

(12) United States Patent
Archer et al.

(10) Patent No.: US 8,323,903 B2
(45) Date of Patent: *Dec. 4, 2012

(54) ANTIBODY COMPLEXES AND METHODS FOR IMMUNOLABELING

(75) Inventors: Robert A. Archer, Eugene, OR (US); Joseph M. Beechem, Eugene, OR (US); David C. Hagen, Eugene, OR (US); Richard P. Haugland, Eugene, OR (US); Rosaria P. Haugland, Eugene, OR (US)

(73) Assignee: Life Technologies Corporation, Carlsbad, CA (US)

(*) Notice: Subject to any disclaimer, the term of this patent is extended or adjusted under 35 U.S.C. 154(b) by 315 days.

This patent is subject to a terminal disclaimer.

(21) Appl. No.: 10/118,204

(22) Filed: Apr. 5, 2002

(65) Prior Publication Data

US 2003/0073149 A1 Apr. 17, 2003

Related U.S. Application Data

(60) Provisional application No. 60/329,068, filed on Oct. 12, 2001, provisional application No. 60/369,418, filed on Apr. 1, 2002.

(51) Int. Cl.
*G01N 33/53* (2006.01)

(52) U.S. Cl. .......................................... 435/7.1; 436/518

(58) Field of Classification Search .................. 435/5, 6, 435/9.1, 7.9, 91.2, 7.1; 436/536, 537, 540, 436/91, 814

See application file for complete search history.

(56) References Cited

U.S. PATENT DOCUMENTS

| 3,996,345 A | 12/1976 | Ullman et al. |
| 4,174,384 A | 11/1979 | Ullman et al. |
| 4,196,265 A | 4/1980 | Koprowski et al. |
| 4,199,559 A | 4/1980 | Ullman et al. |
| 4,235,869 A * | 11/1980 | Schwarzberg ................ 436/512 |
| 4,261,968 A | 4/1981 | Ullman et al. |
| 4,384,042 A | 5/1983 | Miike et al. |
| 4,469,787 A | 9/1984 | Woods et al. |

(Continued)

FOREIGN PATENT DOCUMENTS

EP 0150905 A2 8/1985

(Continued)

OTHER PUBLICATIONS

Owen et al. The genetic engineering of monoclonal antibodies J. Immuno. Methods 1994 168: 149-165.*

(Continued)

*Primary Examiner* — Jacob Cheu
(74) *Attorney, Agent, or Firm* — Life Technologies Corp.

(57) ABSTRACT

The present invention provides novel immunolabeling complexes and certain components of such complexes, as well as methods of preparing and using such complexes, and kits for use in preparing labeling proteins and for immunolabeling. The pre-formed immunolabeling complexes of the invention comprise both a target-binding antibody and a labeling protein that contains covalently attached labels, where the labeling protein binds selectively and with high affinity to a selected region of the target-binding antibody. Novel labeling proteins of the invention include non-antibody peptides and proteins, such as a complex of protein G and a labeled albumin, and monovalent antibody fragments, such as labeled Fab fragments of an anti-Fc antibody. In methods of the invention, the preformed immunolabeling complexes are added to the sample alone or in combination, for purposes of labeling and optionally detecting the target of interest.

33 Claims, 7 Drawing Sheets

U.S. PATENT DOCUMENTS

| | | | |
|---|---|---|---|
| 4,481,298 A | 11/1984 | Cone et al. | |
| 4,520,110 A | 5/1985 | Stryer et al. | |
| 4,542,104 A | 9/1985 | Stryer et al. | |
| 4,603,209 A | 7/1986 | Tsien et al. | |
| 4,603,290 A | 7/1986 | Shinomiya et al. | |
| 4,642,334 A | 2/1987 | Moore et al. | |
| 4,659,678 A | 4/1987 | Forrest et al. | |
| 4,661,444 A | 4/1987 | Li et al. | |
| 4,665,024 A | 5/1987 | Mansour | |
| 4,714,763 A | 12/1987 | Theodoropulos | |
| 4,735,210 A | 4/1988 | Goldenberg | |
| 4,737,579 A * | 4/1988 | Hellstrom et al. | 530/388.85 |
| 4,774,339 A | 9/1988 | Haugland et al. | |
| 4,810,636 A | 3/1989 | Corey et al. | |
| 4,812,409 A | 3/1989 | Babb et al. | |
| 4,849,362 A | 7/1989 | Demarinis et al. | |
| 4,859,582 A | 8/1989 | Stryer et al. | |
| 4,868,109 A | 9/1989 | Lansdorp | |
| 4,891,313 A | 1/1990 | Berger et al. | |
| 4,945,171 A | 7/1990 | Haugland et al. | |
| 4,946,778 A | 8/1990 | Ladner et al. | |
| 4,981,977 A | 1/1991 | Southwick et al. | |
| 5,011,771 A * | 4/1991 | Bellet et al. | 435/7.94 |
| 5,034,506 A | 7/1991 | Summerton et al. | |
| 5,055,556 A | 10/1991 | Stryer et al. | |
| 5,082,928 A | 1/1992 | Best | |
| 5,084,398 A | 1/1992 | Huston et al. | |
| 5,089,419 A * | 2/1992 | Kuniyuki | 436/65 |
| 5,132,432 A | 7/1992 | Haugland et al. | |
| 5,151,507 A | 9/1992 | Hobbs, Jr. et al. | |
| 5,187,085 A | 2/1993 | Lee | |
| 5,187,288 A | 2/1993 | Kang et al. | |
| 5,196,306 A | 3/1993 | Bobrow et al. | |
| 5,208,148 A | 5/1993 | Haugland et al. | |
| 5,227,487 A | 7/1993 | Haugland et al. | |
| 5,229,302 A | 7/1993 | Miyazaki et al. | |
| 5,242,805 A | 9/1993 | Haugland et al. | |
| 5,248,782 A | 9/1993 | Haugland et al. | |
| 5,268,486 A | 12/1993 | Waggoner et al. | |
| 5,274,113 A | 12/1993 | Kang et al. | |
| 5,281,521 A | 1/1994 | Trojanowski et al. | |
| 5,292,658 A | 3/1994 | Cormier et al. | |
| 5,316,906 A | 5/1994 | Haugland et al. | |
| 5,360,895 A | 11/1994 | Hainfeld et al. | |
| 5,362,628 A | 11/1994 | Haugland et al. | |
| 5,376,557 A | 12/1994 | Schmitt | |
| 5,418,155 A | 5/1995 | Cormier et al. | |
| 5,433,896 A | 7/1995 | Kang et al. | |
| 5,442,045 A | 8/1995 | Haugland et al. | |
| 5,443,953 A | 8/1995 | Hansen et al. | |
| 5,443,986 A | 8/1995 | Haugland et al. | |
| 5,451,343 A | 9/1995 | Neckers et al. | |
| 5,459,276 A | 10/1995 | Kuhn et al. | |
| 5,486,616 A | 1/1996 | Waggoner et al. | |
| 5,501,980 A | 3/1996 | Katerinopoulos et al. | |
| 5,558,991 A | 9/1996 | Trainor | |
| 5,561,045 A | 10/1996 | Dorval et al. | |
| 5,565,332 A * | 10/1996 | Hoogenboom et al. | 435/69.1 |
| 5,569,587 A | 10/1996 | Waggoner | |
| 5,569,766 A | 10/1996 | Waggoner et al. | |
| 5,576,424 A | 11/1996 | Mao et al. | |
| 5,583,001 A | 12/1996 | Bobrow et al. | |
| 5,585,243 A | 12/1996 | Aster et al. | |
| 5,602,240 A | 2/1997 | De Mesmaeker et al. | |
| 5,627,027 A | 5/1997 | Waggoner | |
| 5,630,924 A * | 5/1997 | Fuchs et al. | 204/601 |
| 5,635,603 A | 6/1997 | Hansen et al. | |
| 5,637,258 A | 6/1997 | Goldburt | |
| 5,679,519 A * | 10/1997 | Oprandy | 435/6 |
| 5,731,158 A | 3/1998 | Bobrow et al. | |
| 5,736,137 A | 4/1998 | Anderson | |
| 5,736,330 A | 4/1998 | Fulton | |
| 5,766,941 A | 6/1998 | Cormier et al. | |
| 5,773,236 A | 6/1998 | Diwu et al. | |
| 5,789,157 A | 8/1998 | Jensen et al. | |
| 5,798,276 A | 8/1998 | Haugland et al. | |
| 5,798,441 A | 8/1998 | Cormier et al. | |
| 5,808,044 A | 9/1998 | Brush et al. | |
| 5,830,912 A | 11/1998 | Gee et al. | |
| 5,846,737 A | 12/1998 | Kang | |
| 5,869,274 A | 2/1999 | Tsao et al. | |
| 5,872,221 A * | 2/1999 | Martin et al. | 530/388.85 |
| 5,877,310 A | 3/1999 | Reddington et al. | |
| 5,891,741 A | 4/1999 | Siiman et al. | |
| 5,948,386 A | 9/1999 | Katti | |
| 5,969,135 A | 10/1999 | Ramasamy | |
| 5,969,157 A | 10/1999 | Vicenzi | |
| 5,981,180 A | 11/1999 | Chandler et al. | |
| 5,994,143 A * | 11/1999 | Bieniarz et al. | 436/9.1 |
| 6,002,003 A | 12/1999 | Shen et al. | |
| 6,004,536 A | 12/1999 | Leung et al. | |
| 6,008,373 A | 12/1999 | Waggoner et al. | |
| 6,030,773 A | 2/2000 | Agnello | |
| 6,043,025 A | 3/2000 | Minden et al. | |
| 6,080,868 A | 6/2000 | Lee et al. | |
| 6,114,038 A | 9/2000 | Castro et al. | |
| 6,127,134 A | 10/2000 | Minden et al. | |
| 6,130,094 A | 10/2000 | Waggoner et al. | |
| 6,130,101 A | 10/2000 | Mao et al. | |
| 6,133,445 A | 10/2000 | Waggoner et al. | |
| 6,146,836 A * | 11/2000 | Barlow | 435/7.1 |
| 6,150,123 A | 11/2000 | Cosma et al. | |
| 6,162,931 A | 12/2000 | Gee et al. | |
| 6,166,202 A | 12/2000 | Simmonds et al. | |
| 6,179,912 B1 | 1/2001 | Barbera-Guillem et al. | |
| 6,214,568 B1 * | 4/2001 | Endl et al. | 435/7.4 |
| 6,221,602 B1 | 4/2001 | Barbera-Guillem et al. | |
| 6,229,055 B1 | 5/2001 | Klaubert et al. | |
| 6,261,779 B1 | 7/2001 | Barbera-Guillem et al. | |
| 6,274,324 B1 | 8/2001 | Davis et al. | |
| 6,287,785 B1 | 9/2001 | Shinoki et al. | |
| 6,303,755 B1 | 10/2001 | Deo et al. | |
| 6,306,610 B1 | 10/2001 | Bawendi et al. | |
| 6,326,144 B1 | 12/2001 | Bawendi et al. | |
| 6,339,392 B1 | 1/2002 | Ashihara et al. | |
| 6,342,588 B1 | 1/2002 | Osbourn et al. | |
| 6,348,596 B1 | 2/2002 | Lee et al. | |
| 6,352,830 B1 | 3/2002 | Crabtree et al. | |
| 6,399,392 B1 | 6/2002 | Haugland et al. | |
| 6,475,808 B1 * | 11/2002 | Wagner et al. | 436/518 |
| 6,482,655 B1 | 11/2002 | Wei et al. | |
| 6,541,618 B1 | 4/2003 | Lee et al. | |
| 6,787,638 B1 * | 9/2004 | Watkins et al. | 530/388.85 |
| 6,855,551 B2 | 2/2005 | Bawendi et al. | |
| 6,972,326 B2 | 12/2005 | Haugland et al. | |
| 6,974,873 B2 | 12/2005 | Leung et al. | |
| 6,977,305 B2 | 12/2005 | Leung et al. | |
| 2002/0034771 A1 | 3/2002 | Frank et al. | |
| 2002/0064794 A1 | 5/2002 | Leung et al. | |
| 2002/0077487 A1 | 6/2002 | Leung et al. | |
| 2002/0081635 A1 | 6/2002 | Thomas et al. | |
| 2002/0094534 A1 | 7/2002 | Greene et al. | |
| 2002/0132254 A1* | 9/2002 | Twu | 435/6 |
| 2003/0073149 A1 | 4/2003 | Archer et al. | |
| 2007/0269902 A1 | 11/2007 | Beechem et al. | |
| 2009/0124511 A1 | 5/2009 | Archer et al. | |

FOREIGN PATENT DOCUMENTS

| | | |
|---|---|---|
| EP | 0 205 198 | 4/1986 |
| EP | 0269451 | 6/1988 |
| EP | 0 389 301 | 3/1990 |
| EP | 0 307 754 | 4/1990 |
| EP | 0 310 132 | 10/1990 |
| EP | 0 396 505 | 4/1991 |
| EP | 0 368 674 | 10/1991 |
| EP | 0 178 125 B1 | 8/1992 |
| EP | 0509718 * | 10/1992 |
| EP | 0566 205 A1 | 4/1993 |
| EP | 0 292 810 | 8/1993 |
| EP | 0566205 | 10/1993 |
| EP | 0603107 * | 10/1993 |
| EP | 0 291 086 | 4/1994 |
| EP | 0 629 857 | 6/1996 |
| EP | 0794261 | 9/1997 |
| EP | 0 918 218 A2 | 3/1999 |
| EP | 0 989 406 | 3/2000 |
| EP | 0 599 803 | 4/2000 |

| | | |
|---|---|---|
| EP | 1054258 | 11/2000 |
| EP | 1065250 | 8/2004 |
| EP | 1442302 | 8/2004 |
| GB | 2302094 A | 1/1997 |
| JP | 60082966 | 5/1985 |
| JP | 62174029 | 7/1987 |
| JP | 01-131458 | 5/1989 |
| JP | 02-076600 | 3/1990 |
| JP | 2000310638 | 11/2000 |
| JP | 2001059845 | 3/2001 |
| WO | WO 89/06799 | 7/1989 |
| WO | WO 89/12231 | 12/1989 |
| WO | WO-9102547 | 3/1991 |
| WO | WO 91/18291 | 11/1991 |
| WO | WO 97/17610 | 5/1997 |
| WO | WO-9717610 | 5/1997 |
| WO | WO-97/40104 | 10/1997 |
| WO | WO-99/51702 | 10/1999 |
| WO | WO 99/67642 | 12/1999 |
| WO | WO-01/21624 | 3/2001 |
| WO | WO-0226891 | 4/2002 |
| WO | WO-03/030817 | 4/2003 |

OTHER PUBLICATIONS

Gandhi et al., Tubercle, 67, 219-224 (1986).
March et al., Rheumatology, 6, 155-160 (1986).
Tarkowski et al., Journal of Immunological Methods, 72, 451- 459 (1984).
Hansen et al., Scand. J. Clin. Lab. Invest., 43, 513-519, (1983).
Coulter et al., Journal of Immunological Methods, 59, 199-203 (1983).
Delespesse et al., Horm. Metab. Res., 8, 50-54 (1976).
Tarkowski et al., Journal of Immunological Methods, 58, 171-182, (1983).
Springer et al., Hybridoma, vol. 1 No. 3. 257-273, (1982).
Butler et al., Journal of Immunological Methods, 20, 365-383, (1978).
Naot et al., Journal of Clinical Microbiology, vol. 14, No. 1, 73-78, (1981).
Barbara et al., J. Gen. Virol., 58, 315-322, (1982).
Bellefontaine et al., Applied Biochemistry and Biotechnology, 48, 117-123, (1994).
Lamoyi, Methods in Enzymology 121, 652-663, (1986).
Muratsugu et al., Chem. Pharm. Bul., 40, 501-503 (1992).
Lu et al., The Journal of Histochemistry & Cytochemistry, 46, 977-983 (1998).
Poglitsch et al., Biochemistry, 29, 248-254, (1990).
Relf et al., Anal. Chem., 66, 4027-4033, (1994).
Silver et al., Clin. Chem., 32/7, 1303-1306 (1986).
Hsu et al., The Journal of Histochemistry & Cytochemistry, 29, 1349-1353 (1981).
Sternberger et al., The Journal of Histochemistry & Cytochemistry, 18, 315-333 (1970).
Rubenstein et al., Biochemical and Biophysical Research Communications 47, 846-851 (1972).
Dudich et al., Molecular Immunology, 20, 1267-1272, (1983).
Koksch et al., Journal of Immunological Methods 187, 53-67, (1995).
Pope et al., J. Lab. Clin. Med., 97, 842-853, (1981).
Sheikl et al., Analytical Biochemistry, 283, 33-38, (2000).
Kato et al., The Journal of Immunology, 116, 1554-1560, (1976).
Kaplan et al., Veterinary Immunology and Immunopathology, 4, 307-317, (1983).
Bacigalupo et al., Fresenius J. Anal Chem., 370, 82-87, (2001).
Friedman et al., Journal of Clinical Microbiology, 9, 1-10, (1979).
Ullman et al., Methods in Enzymology, 74, 28-60, (1981).
Kato et al., FEBS Letters, 56, 370-372, (1975).
Attiya et al., Electrophoresis, 23, 750-758, (2002).
Zuk et al., Clin. Chem., 25, 1554-1560 (1979).
Harris et al., Journal of Immunological Methods, 8, 203-212, (1975).
Nitta et al., Eur. J. Immumnol., 19, 1437-1441 (1989).
Gandhi et al., Transactions of the Royal Society of Tropical Medicine and Hygiene, 81, 183-185, (1987).
Goroff et al., Journal of Immunology, 140, 2919-2924 (1988).
Gibbons et al., Clin. Chem. 27, 1602-1608, (1981).
Lydyard et al., Scand. J. Immunol., 31, 33-43, (1990).
Hsu et al., American Society of Clinical Pathologists, 75, 816-821, (1981).
Hsu et al., American Society of Clinical Pathologists, 80, 429-435, (1983).
Singhet al., Journal of C° linical Pathology, 31, 963-973, (1978).
Kato et al., J. Biochem., 78, 423-425 (1975).
Brelje, et al., Methods in Cell Biology 38, 97-181, especially 111-118 (1993).
Clancy et al., Journal of Neuroscience Methods 83, 97-102 (1998).
Tagliaferro et al., Journal of Neuroscience Methods, 77, 191-197 (1997).
Molecular Probes Handbook of Fluorescent Probes and Research Chemicals by Richard P. Haugland, $6^{th}$ Ed., (1996), and its subsequent $7^{th}$ edition and $8^{th}$ edition updates issued on CD Rom in Nov. 1999 and May 2001.
Sun et al., J. Immunol. Meth. 152, 43-48(1992).
Eliasson et al., J. Biol. Chem. 263, 4323-4327 (1988).
Eliasson et al., J. Immunol. 142, 575-581 (1989).
Schena (Ed.), Microarray Biochip Technology, (2000).
Haab et al., Genome Biology, 2, 4.1 (2001).
Ponder, "Cell Marking Techniques and Their Aplicaiton," Mammalian Development: A Practical Approach, Monk (ed.), 115 (1987.
Radiolabeled Monoclonal Antibodies for Imaging and Therapy, Plenum Press (1988).
"Medical Applications of Radioisotopes," in Remington's Pharmaceutical Sciences, 18th Edition, Gennaro et al. (eds.) Mack Publishing Co., 624 (1990).
"Clinical Use of Monoclonal Antibodies," in Biotechnology and Pharmacy, Pezzuto et al. (eds.), Chapman & Hall, 227 (1993).
Fraker et al., Biochem. Biophys. Res. Commun. 80, 849-857 (1978).
Camera et al., J. Nucl. Med. 35, 882 -889 (1994).
Remington's Pharmaceutical Sciences, 18th Ed. (1990).
Sherwood et al., Biotechnology 10, 1446 (1992).
Saltzman et al., Biophysical J. 55, 163 (1989).
Current Protocols in Cell Biology, 16.4.1-16.4.10 (2000).
Current Protocols in Immunology 2.4.1-9 (1995).
ILAR Journal 37, 93 (1995).
Surolia et al., Trends Biochem. Sci. 7, 74 (1982).
Notani et al., J. Histochem. Cytochem. 27, 1438 (1979).
Goding, J. Immunol. Meth. 20, 241 (1978).
J. Immunol. Meth. 127, 215 (1990).
Bjorck et al., J. Immunol. 133, 969 (1984).
Hanson et al., Electrophoresis 22, 950 (2001).
Beisker et al., Cytometry 8, 235 (1987).
J. Histochem. Cytochem. 45, 327 (1997).
Brinkley, Bioconjugate Chem. 3, 2 (1992).
Beverloo, et al., Anal. Biochem. 203, 326-34 (1992).
Bird et al., Science 242, 423 (1988).
J. Histochem. Cytochem. 34, 703 (1986).
Appl. Immunohistochem. Molecul. Morphol. 9, 176 (2001).
J. Histochem. Cytochem. 43, 193 (1995).
Huston et al., Proc. Natl. Acad. Sci. USA 85, 5879 (1988).
Ward, et al., Nature 341, 544 (1989).
Haugland et al., Meth. Mol. Biol. 45, 205 (1995).
Haugland, Meth. Mol. Biol. 45, 223 (1995).
Haugland, Meth. Mol. Biol. 45, 235 (1995).
Haugland, Current Protocols in Cell Biol. 16.5.1-16.5.22 (2000).
Langone, Adv. Immunol. 32, 157 (1982).
J. Histochem Cytochem 39, 741 (1991).
Application Serial No. PCT/01/30404.
Chemicon International Product Literature.
Nanoprobes Product Information Sheet.
Nanoprobes Product Literature.
Pierce Biotechnology Product Literature.
Rockland Immunochemcials for Research Product Literature.
Eichmuller, S et al., "A New Method for Double Immunolabelling with Primary Antibodies from Identical Species", Journal of Immunological Methods, Elsevier Science Publishers, B.V., Amsterdam, NL, vol. 190, No. 2,(Apr. 19, 1996),255-265.
Ferri, Gian-Luca et al., "Quadruple Immunofluorescence: A Direct Visualization method", Journal of Histochemistry and Cytochemistry, vol. 45, No. 2,(1997),155-158.

Gonatas, N K., et al., "Ultrastructural Autoradiographic Detection of Intracellular Immunoglobulins With Iodinated Fab Fragments of Antibody. The Combined use of Ultrastructural Autoradiography and Peroxidase Cytochemistry for the Detection of Two Antigens (Double Labeling)", Journal of Histochemistry and Cytochemistry, vol. 22, No. 11, Database Embase, Database Accession No. EMB-1975166176, Abstract,(1974),999-1009.

Kachidian, P et al., "Dual Immunocytochemistry Using Iodine-125-Labeled Protein A A new Electron Microscopic Technique Applied to the Investigation of Chemical Connectivity and Axonal Transmitter Co-Localization in the Brain", Journal of Neuroscience Methods, vol. 38, No. 2-3,(1991),115-128.

Kruger, N J., "Detection of Polypeptides on Immunoblots Using Secondary Antibodies or Protein A", Methods in Molecular Biology (Clifton, N.J.), vol. 32,(1994),215-226.

Negoescu, Adrien et al., "F(ab) Secondary Antibodies: A General Method for Double Immunolabeling With Primary Antisera From the Same Species. Effciency Control by Chemiluminescence", Journal of Histochemistry and Cytochemistry, vol. 42, No. 3,(1994),433-437.

Van Der Loos, Chris M., et al., "The Animal Research Kit (ARK) can be Used in a Multistep Double Staining Method for Human Tissue Specimens", Journal of Histochemistry and Cytochemistry, vol. 48, No. 10,(Oct. 2000),1431-1437.

Wessel, G M., et al., "Two Embryonic Tissue-Specific Molecules identified by a Double-Label Immunofluorescence Technique for Monoclonal Antibodies", Journal of Histochemistry and Cytochemistry,(1986),703-706.

U.S. Appl. No. 10/467,550, "Non-Final Rejection mailed Sep. 12, 2007.".

10181177.6, "European Search Report Mailed on Feb. 3, 2011".

U.S. Appl. No. 12/047,131, "Office Action Mailed Jul. 8, 2010".

U.S. Appl. No. 12/047,131, "Office Action Mailed Oct. 20, 2009".

U.S. Appl. No. 12/047,131, "Office Action Mailed Jun. 18, 2009".

U.S. Appl. No. 12/047,131, "Response to Jun. 18, 2009 Office Action filed Sep. 4, 2009".

EP02768949, "European Search Report mailed Feb. 23, 2007".

EP02768949, "Supplemental European Search Report mailed Feb. 28, 2007".

EP09163588, "European Search report mailed on Jan. 15, 2010".

PCT/US02/31416, "International Preliminary Report on Patentability mailed Aug. 26, 2003".

PCT/US02/31416, "International Search Report mailed Jul. 16, 2003".

Brown, Jeremy K. et al., "Primary Antibody-Fab Fragment Complexes: A Flexible Alternative to Traditional Direct and Indirect Immunolabeling Techniques", Journal of Histochemistry & Cytochemistry vol. 52, No. 9 2004 , 1219-1230.

Dos Remedios, Cristobal G. et al., "Fluorescence Resonance Energy Transfer Spectroscopy is a Reliable "Ruler" for Measuring Structural Changes in Proteins", Journal of Structural Biology, vol. 115 1995 , 175-185.

Gorevic, Peter D. et al., "Immunoglobulin G (IgG)", Methods in Enzymology vol. 116 1985, 3-25.

Haugland, Richard P., "Handbook of Fluorescent Probes and Research Products", Ch 1-3.3 Molecular Probes, Inc/Invitrogen, 2002 2002, 11-118.

Ino, Hidetoshi , "Application of Antigen Retrieval by Heating for Double-label Fluorescent Immunohistochemistry with Identical Species-derived Primary Antibodies", Journal of Histochemistry & Cytochemistry 2004, 1209-1217.

Kricka, L. J. et al., "Detection of Energy Transfer and Fluorescence Quenching", Nonisotopic DNA Probe Techniques San Diego: Academic Press, Inc. 1992, 311-353.

Lindgren, A et al., "Optimisation of a heterogeneous non-competitive flow immunoassay comparing fluorescein, peroxidase and alkaline phosphatase as labels", Journal of Immunological Methods vol. 211 1998, 33-42.

Matayoshi, et al., "Novel Fluoregenic Substrates for Assaying Retroviral Proteases by Resonance Energy Transfer", Science, vol. 247, Feb. 23, 1990, 954-958.

Nato, Advanced Study Institute on Radiolabeled Monoclonal Antibodies for Imaging and Therapy Radiolabeled Monoclonal Antibodies for Imaging and Therapy, Srivasta (ed.) 1988.

Neuweiler, H. et al., "Detection of individual p53-autoantibodies by using quenched peptide-based molecular probes", Angewandte Chemie International Edition in English vol. 41 No. 24 2002, 4769-73.

Selvin, Paul R., "Fluorescence Resonance Energy Transfer", Methods in Enzymology, vol. 246 1995, 300-334.

Shea, Michael et al., "High-performance liquid chromatographic measurement of exogenous thiosulfate in urine and plasma", Analytical Biochemistry vol. 140, No. 2 Aug. 1, 1984, 589-594.

Stirling, John W. , "Immuno- and Affinity Probes for Electron Microscopy: A Review of Labeling and Preparation Techniques", Journal of Histochemistry and Cytochemistry vol. 38, No. 2 1990, 145-158.

Togawa, T. et al., "High performance liquid chromatographic determination of bound sulfide and sulfite and thiosulfate at their low levels in human serum by pre-column fluorescence derivatization with monobromobimane", Chem pharm Bull (Tokyo) 40(11): 1992, 3000-4.

Tyagi, et al., "Molecular Beacons: Probes that Fluoresceupon Hybridization", Nature Biotechnology, vol. 14, Tyagi Sanjay and Fred Russell Kramer Mar. 1996 , 303-308.

Tyagi, Sanjay et al., "Multicolor molecular beacons for allele discrimination", Nature Biotechnology, vol. 16 1998, 49-53.

Ullman, E. F. et al., "Fluorescent excitation transfer immunoassay. A general method for determination of antigens", J Biol Chem Int Ed Engl 41(24) 1976.

Wei, A. P. et al., "Antibody-mediated fluorescence enhancement based on shifting the intramolecular dimer<--->monomer equilibrium of fluorescent dyes", Anal Chem 66(9) 1994, 1500-6.

Wei, A. P. et al., "Bifluorophoric molecules as fluorescent beacons for antibody-antigen binding", J Mol Recognit 15(5) 2002, 311-20.

Wu, Pengguang et al., "Resonance Energy Transfer: Methods and Applications", Analytical Biochemistry vol. 218, No. 1 1994 , 1-13.

Zhang, Ji-Hu et al., "A Simple Statistical Parameter for Use in Evaluation and Validation of High Throughout Screening Assays", Journal of Biomolecular Screening vol. 4, No. 2 1999, 67-73.

Zhang, Y-Z. et al., "Cell fusion Monitored with Long-Term Cell Tracking, Fluorescent Probes", Molecular Biology of the Cell vol. 3, Abstract# 525 Nov. 1992, 90a.

* cited by examiner

ANTIBODY COMPLEXES AND METHODS FOR IMMUNOLABELING

CROSS-REFERENCE TO RELATED APPLICATIONS

This application claims priority to provisional applications, Ser. No. 60/329,068, filed Oct. 12, 2001 and provisional application No. 60/369,418 filed Apr. 1, 2002, which disclosures are herein incorporated by reference.

FIELD OF INVENTION

The present invention relates to novel immunolabeling compositions and methods for use in the detection and measurement of one or more targets in a biological sample. The invention has applications in the fields of molecular biology, cell biology screening, immunohistochemistry, diagnostics, and therapeutics.

BACKGROUND OF THE INVENTION

Immunolabeling is a method for qualitative or quantitative determination of the presence of a target in a sample, wherein antibodies are utilized for their specific binding capacity. The antibodies form a complex with the target (antigen), wherein a detectable label is present on the antibody or on a secondary antibody. The detectable label is a key feature of immunolabeling, which can be detected directly or indirectly. The label provides a measurable signal by which the binding reaction is monitored providing a qualitative and/or quantitative measure of the degree of binding. The relative quantity and location of signal generated by the labeled antibodies can serve to indicate the location and/or concentration of the target. The label can also be used to select and isolate labeled targets, such as by flow sorting or using magnetic separation media. Examples of labels include but are not limited to radioactive nucleotides ($^{125}I$, $^3H$, $^{14}C$, $^{32}P$), chemiluminescent, fluorescent, or phosphorescent compounds (e.g., dioxetanes, xanthene, or carbocyanine dyes, lanthanide chelates), particles (e.g., gold clusters, colloidal gold, microspheres, quantum dots), and enzymes (e.g., peroxidases, glycosidases, phosphatases, kinases). Ideally, the label is attached to the antibody in a manner that does not perturb the antibody's binding characteristics but enables the label to be measured by an appropriate detection technology. The choice of labels is influenced by factors such as ease and sensitivity of detection, equipment availability, background in the sample (including other labels) and the degree to which such labels are readily attached to the particular antibody. Both direct and indirect labeling of antibodies are utilized for immunolabeling. Direct labeling utilizes only a primary antibody, i.e. the antibody specific for the target, bound to the label. In contrast, indirect labeling utilizes a secondary antibody bound to the label, which is specific for the primary antibody, e.g. a goat anti-rabbit antibody. The principal differences in immunolabeling methods and materials reside in the way that the label is attached to the antibody-antigen complex, the type of label that is used, and the means by which the antibody-antigen complex is detected.

Limitations for direct labeling primary antibodies include the need for buffers free of primary amines, or carrier proteins such as bovine serum albumin (BSA), and other compounds such as tris-(hydroxymethyl)aminomethane (TRIS), glycine, and ammonium ions. These materials are, however, common components in antibody buffers and purification methods, and it may not be possible or feasible to remove them prior to the coupling reaction. In particular, many monoclonal antibodies are available only as ascites fluid or in hybridoma culture supernatants, or diluted with carrier proteins, such as albumins. Thus, direct labeling of antibodies in ascites fluid or other medias containing interfering compounds is not attainable.

The indirect immunolabeling method typically involves a multi-step process in which an unlabeled first antibody (typically a primary antibody) is directly added to the sample to form a complex with the antigen in the sample. Subsequently, a labeled secondary antibody, specific for the primary antibody, is added to the sample, where it attaches noncovalently to the primary antibody-antigen complex. Alternatively, a detectable label is covalently attached to an immunoglobulin-binding protein such as protein A and protein G to detect the antibody-antigen complex that has previously been formed with the target in the sample. Using ligands, such as streptavidin, that are meant to amplify the detectable signal also expands this cascade binding.

Indirect immunolabeling often results in false positives and high background. This is due to the fact that secondary antibodies, even when purified by adsorption against related species, nevertheless can exhibit significant residual cross-reactivity when used in the same sample. For example, when mouse tissue is probed with a mouse monoclonal antibody, the secondary antibody must necessarily be a labeled anti-mouse antibody. This anti-mouse antibody will detect the antibody of interest but will inevitably and additionally detect irrelevant, endogenous mouse immunoglobulins inherent in mouse tissue. This causes a significant background problem, especially in diseased tissues, which reduces the usefulness and sensitivity of the assay. Thus, the simultaneous detection of more than one primary antibody in a sample without this significant background interference depends on the availability of secondary antibodies that 1) do not cross-react with proteins intrinsic to the sample being examined, 2) recognize only one of the primary antibodies, and 3) do not recognize each other (Brelje, et al., METHODS IN CELL BIOLOGY 38,97-181, especially 111-118 (1993)).

To address the background problem in indirect labeling, a number of strategies have been developed to block access of the anti-mouse secondary antibodies to the endogenous mouse immunoglobulins. One such strategy for blocking involves complexing the primary antibody with a selected biotinylated secondary antibody to produce a complex of the primary and secondary antibodies, which is then mixed with diluted normal murine serum (Trojanowski et al., U.S. Pat. No. 5,281,521 (1994)). This method is limited by the necessity to utilize an appropriate ratio of primary-secondary complex. Too low a ratio of primary-secondary complex will cause a decrease in specific staining and increased background levels due to the uncomplexed secondary anti-mouse antibody binding to endogenous mouse antibodies. However, the ability of a whole IgG antibody (as was used in the referenced method) to simultaneously bind and crosslink two antigens results in too high a ratio, causing the complex to precipitate or form complexes that are too large to penetrate into the cell or tissue.

Another strategy for blocking access to endogenous immunoglobulins in the sample involves pre-incubating the sample with a monovalent antibody, such as Fab' fragments, from an irrelevant species that recognize endogenous immunoglobulins. This approach requires large quantities of expensive Fab' fragments and gives mixed results and adds at least two steps (block and wash) to the overall staining procedure. The addition of a cross-linking reagent has resulted in improved reduction of background levels (Tsao, et al., U.S. Pat. No. 5,869, 274 (1997)) but this is problematic when used with fluorophore-labeled antibodies. The cross-linking causes an increase in the levels of autofluorescence (J. Neurosci. Meth. 83, 97 (1998); Mosiman et al., Methods 77, 191 (1997); Commun. Clin. Cytometry 30, 151 (1997); Beisker et al., Cytometry 8, 235 (1987)) and thus the background. In addition, pre-incubation with a cross-linking reagent often masks or prevents the antibody from binding to its antigen (J. Histochem. Cytochem. 45, 327 (1997); J. Histochem. Cytochem. 39, 741 (1991); J. Histochem. Cytochem. 43, 193 (1995); Appl. Immunohistochem. Molecul. Morphol. 9, 176 (2001)).

In a variation of this blocking strategy, a multi-step sequential-labeling procedure is used to overcome the problems of cross-reactivity. The sample is incubated with a first antibody to form a complex with the first antigen, followed by incubation of the sample with a fluorophore-labeled goat Fab anti-mouse IgG to label the first antibody and block it from subsequently complexing when the second antibody is added. In the third step, a second mouse antibody forms a complex with the second antigen. Being blocked from cross-reacting with the first antibody, the second mouse antibody is detected with a standard indirect-labeling method using a goat anti-mouse antibody conjugated to a different fluorescent dye (J. Histochem. Cytochem. 34, 703 (1986)). This process is complex in that it requires multiple incubation steps and washing steps and it still cannot be used with mouse antibodies to probe mouse tissue.

Another blocking method is disclosed in the animal research kit (ARK) developed by DAKO. In this kit, a primary antibody is complexed with biotin-labeled goat Fab anti-mouse IgG and excess free Fab is blocked with normal mouse serum. However, since the Fab used in this process is generated from the intact IgG (rather than a selected region) there is a potential for the formation of anti-paratope or anti-idiotype antibodies that will block the antigen-binding site and prevent immunolabeling. The biotinylated antibody also requires subsequent addition of a labeled avidin or streptavidin conjugate for its subsequent visualization.

The present invention is advantageous over previously described methods and compositions in that it provides the benefits of indirect labeling with the easy and flexibility of direct labeling for determination of a desired target in a biological sample. The present invention provides labeled monovalent proteins specific for a target-binding antibody, which are complexed prior to addition with a biological sample. Because these monovalent proteins are not bivalent antibodies, precipitation and cross-linking are not a problem. Therefore the compositions of the present invention can be used with immunologically similar monoclonal or polyclonal antibodies of either an identical isotype or different isotypes. The monovalent labeling proteins are specific for the Fc region of target-binding antibodies, these proteins will not interfere with the binding region of the primary antibody. In addition, the monovalent labeling proteins are not negatively affected by the presence of primary amines like BSA, gelatin, hybridoma culture supernatants or ascites fluid, thus primary antibodies present in these media can be effectively labeled with the labeling proteins of the present invention. Thus, the present invention provides numerous advantages over the conventional methods of immunolabeling.

SUMMARY OF THE INVENTION

Methods and compositions are provided for determining the presence, absence or location of a desired target in a biological sample. The methods initially involve pre-forming the immunolabeling complex, the target-binding antibody and the labeling protein, followed by addition to a biological sample and determination of the desired target. The methods of the invention are broadly applicable to immunolabeling any antigen target in any sample from any origin.

DESCRIPTION OF THE SPECIFIC EMBODIMENTS

I. Definitions

Figure 1:
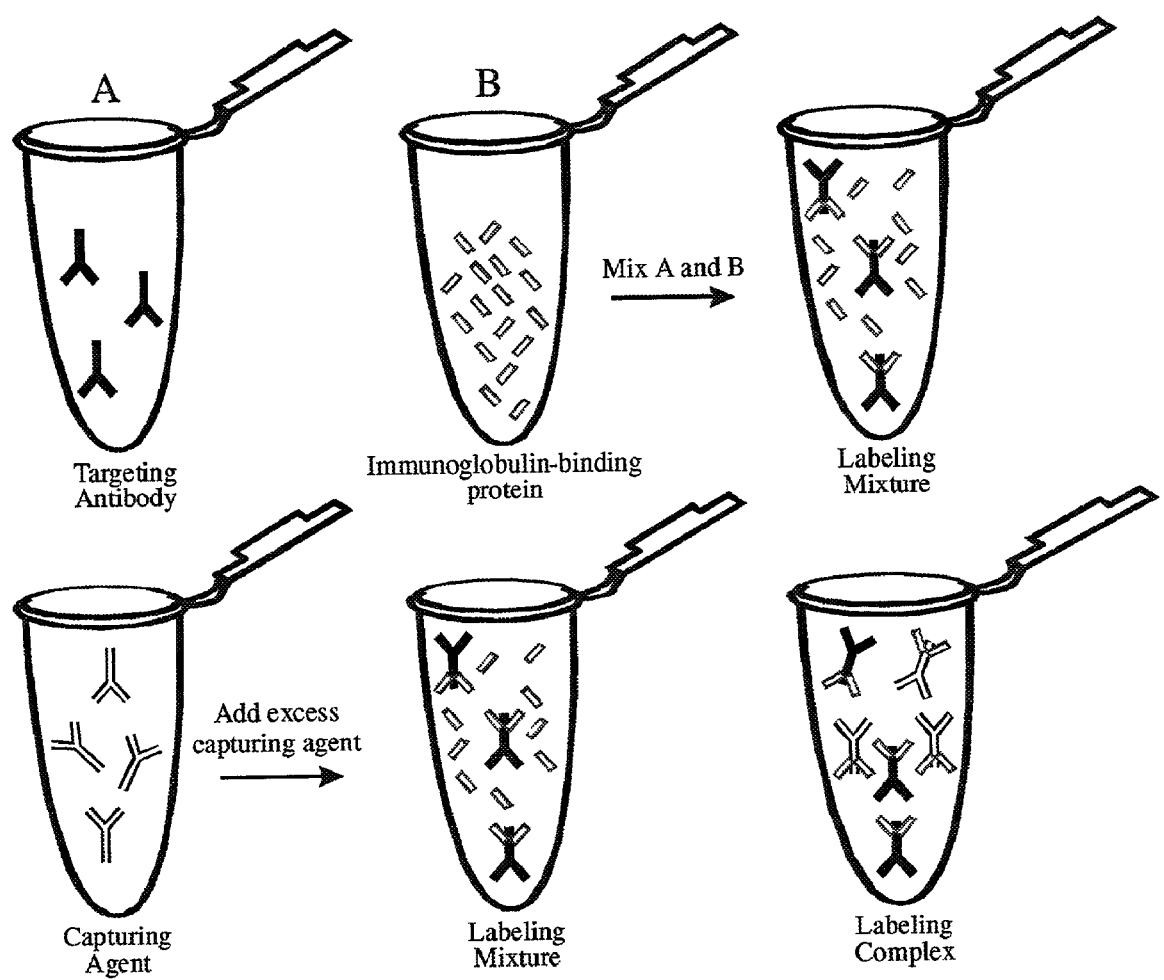
FIG. 1 is a schematic representation of the formation of the immunolabeling complex (target-bindingprotein and labeling protein).

To assist in the understanding of the invention, the following terms, as used herein, are defined below.

"Affinity" is defined as the strength of the binding interaction of two molecules, such as an antigen and its antibody, which is defined for antibodies and other molecules with more than one binding site as the strength of binding of the ligand at one specified binding site. Although the noncovalent attachment of a ligand to antibody is typically not as strong as a covalent attachment, "High affinity" is for a ligand that binds to an antibody having an affinity constant ($K_a$) of greater than $10^4$ $M^{-1}$, typically $10^5$-$10^{11}$ $M^{-1}$; as determined by inhibition ELISA or an equivalent affinity determined by comparable techniques such as, for example, Scatchard plots or using $K_d$/dissociation constant, which is the reciprocal of the $K_a$, etc.

"Antibody" is a protein of the immunoglobulin (Ig) superfamily that binds noncovalently to certain substances (e.g. antigens and immunogens) to form an antibody-antigen complex, including but not limited to antibodies produced by hybridoma cell lines, by immunization to elicit a polyclonal antibody response, by chemical synthesis, and by recombinant host cells that have been transformed with an expression vector that encodes the antibody. In humans, the immunoglobulin antibodies are classified as IgA, IgD, IgE, IgG, and IgM and members of each class are said to have the same isotype. Human IgA and IgG isotypes are further subdivided into subtypes $IgA_1$, and $IgA_2$, and $IgG_1$, $IgG_2$, $IgG_3$, and $IgG_4$. Mice have generally the same isotypes as humans, but the IgG isotype is subdivided into $IgG_1$, $IgG_{2a}$, $IgG_{2b}$, and $IgG_3$ subtypes. Thus, it will be understood that the term "antibody" as used herein includes within its scope (a) any of the various classes or sub-classes of immunoglobulin, e.g., IgG, IgM, IgE derived from any of the animals conventionally used and (b) polyclonal and monoclonal antibodies, such as murine, chimeric, or humanized antibodies. Antibody molecules have regions of amino acid sequences that can act as an antigenic determinant, e.g. the Fc region, the kappa light chain, the lambda light chain, the hinge region, etc. An antibody that is generated against a selected region is designated anti-[region], e.g. anti-Fc, anti-kappa light chain, anti-lambda light chain, etc. An antibody is typically generated against an antigen by immunizing an organism with a macromolecule to initiate lymphocyte activation to express the immunoglobulin protein. The term antibody, as used herein, also covers any polypeptide or protein having a binding domain that is, or is homologous to, an antibody binding domain, including, without limitation, single-chain Fv molecules (scFv), wherein a VH domain and a VL domain are linked by a peptide linker that allows the two domains to associate to form an antigen binding site (Bird et al., Science 242, 423 (1988) and Huston et al., Proc. Natl. Acad. Sci. USA 85, 5879 (1988)). These can be derived from natural sources, or they may be partly or wholly synthetically produced.

"Antibody fragments" refers to fragments of antibodies that retain the principal selective binding characteristics of the whole antibody. Particular fragments are well-known in the art, for example, Fab, Fab', and F(ab')$_2$, which are obtained by digestion with various proteases and which lack the Fc fragment of an intact antibody or the so-called "half-molecule" fragments obtained by reductive cleavage of the disulfide bonds connecting the heavy chain components in the intact antibody. Such fragments also include isolated fragments consisting of the light-chain-variable region, "Fv" fragments consisting of the variable regions of the heavy and light chains, and recombinant single chain polypeptide molecules in which light and heavy variable regions are connected by a peptide linker. Other examples of binding fragments include (i) the Fd fragment, consisting of the VH and CH1 domains; (ii) the dAb fragment (Ward, et al., Nature 341, 544 (1989)), which consists of a VH domain; (iii) isolated CDR regions; and (iv) single-chain Fv molecules (scFv) described above. In addition, arbitrary fragments can be made using recombinant technology that retains antigen-recognition characteristics.

"Antigen" means a molecule that induces, or is capable of inducing, the formation of an antibody or to which an antibody binds selectively, including but not limited to a biological material. Antigen also refers to "immunogen". An antibody binds selectively to an antigen when there is a relative lack of cross-reactivity with or interference by other substances present.

"Biological material" means a material of biological origin or a synthetic variant of a material of biological origin, including but not limited to cells, bodily fluids, membranes, proteins, amino acids, nucleic acids, carbohydrates, lipids, and any polymers or combinations thereof, including natural as well as synthetic polymers that are optionally relatively homogeneous or heterogeneous.

"Biological Sample" refers to any material that may contain a target to which an antibody can bind. Typically, the sample comprises tissue, cell or cells, cell extracts, cell homogenates, purified or reconstituted proteins, recombinant proteins, bodily and other biological fluids, viruses or viral particles, prions, subcellular components, or synthesized proteins. Possible sources of cellular material used to prepare the sample of the invention include without limitation plants, animals, fungi, protists, bacteria, archae, or cell lines derived from such organisms.

"Biotin" means any biotin derivative, including without limitation, substituted and unsubstituted biotin, and analogs and derivatives thereof, as well as substituted and unsubstituted derivatives of caproylamidobiotin, biocytin, desthiobiotin, desthiobiocytin, iminobiotin, and biotin sulfone.

"Biotin-binding protein" means any protein that binds selectively and with high affinity to biotin, including without limitation, substituted or unsubstituted avidin, and analogs and derivatives thereof, as well as substituted and unsubstituted derivatives of streptavidin, ferritin avidin, nitroavidin, nitrostreptavidin, and Neutravidin™ avidin (a de-glycosylated modified avidin having an isoelectric point near neutral).

"Bodily or body fluid" means a fluid substance from the body, including but not limited to, for example, circulating blood and lymph, the chyle, the gastric, pancreatic, and intestinal juices, the saliva, bile, urine, aqueous humor, spinal fluid, muscle serum and ascites.

"Buffer" means a system that acts to minimize the change in concentration of a specific chemical species in solution against addition or depletion of this species.

"Cell or cells" means an autonomous self-replicating unit composed of protoplasm delimited by a cell membrane that may constitute an organism (in the case of unicellular organisms) or be a subunit of multicellular organisms (in which individual cells may be more or less specialized differentiated) for particular functions or plant cells. Cell or cells as used in the instant application also includes cells in cell culture medium, single cells, isolated cells, single-cell organisms; and "portions thereof" including, but not limited to, cell extracts, cell homogenates, cell lysates, and subcellular components.

"Complex" means two or more molecules held together by noncovalent bonding, which are typically noncovalent combinations of biomolecules such as a protein complexed with another protein. In contrast, a protein is covalently labeled with a substance when there is a covalent chemical bond between the substance and the protein.

"Detectable response" means a change in, or occurrence of, a signal that is detectable either by observation or instrumentally. Typically the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction, and electron density.

"Detectably distinct" means the signal is distinguishable or separable by a physical property either by observation or instrumentally. For example, but not limitation, a fluorophore is readily distinguishable, either by spectral characteristics or by fluorescence intensity, lifetime, polarization or photobleaching rate from another fluorophore in the sample, as well as from additional materials that are optionally present.

"Directly detectable" means that the presence of a material or the signal generated from the material is immediately detectable by observation, instrumentation, or film without requiring chemical modifications or additional substances.

"Drug-labeled protein" means a labeling protein of the invention, where instead of a detectable label being attached to the protein, a therapeutic agent or drug is attached. The term drug-labeled protein is used interchangeably with immunoconjugate.

"Enzyme" means a protein molecule produced by living organisms, or through chemical modification of a natural protein molecule, that catalyses chemical reactions of other substances without itself being destroyed or altered upon completion of the reactions. Examples of other substances, include but are not limited to, chemiluminescent, chromogenic, and fluorogenic substances.

"Immunoconjugates" are labeling proteins of the invention, where instead of a detectable label being attached to the protein, a therapeutic agent or drug is attached. The term immunoconjugate is used interchangeably with drug-labeled protein.

"Immunolabeling complex" means an antibody-protein complex made detectable, traceable, or therapeutically useful by incorporation of a detectable label, drug, or therapeutic into the protein that is noncovalently and selectively bound to the antibody.

"Kit" means a packaged set of related components, typically one or more compounds or compositions.

"Label" means a chemical used to facilitate identification and/or quantitation of a target substance. Illustrative labels include labels that can be directly observed or measured or indirectly observed or measured. Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The label can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The label may also take the form of a chemical or biochemical, or an inert particle, including but not limited to colloidal gold, microspheres, quantum dots, or inorganic crystals such as nanocrystals or phosphors (see, e.g., Beverloo, et al., Anal. Biochem. 203, 326-34 (1992)). The term label can also refer to a "tag" or hapten that can bind selectively to a labeled molecule such that the labeled molecule, when added subsequently, is used to generate a detectable signal. For instance, one can use biotin, iminobiotin or desthiobiotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex Red or Amplex Gold (Molecular Probes, Inc.) to detect the presence of HRP. In a similar fashion, the tag can be a hapten or antigen (e.g., digoxigenin), and an enzymatically, fluorescently, or radioactively labeled antibody can be used to bind to the tag. Numerous labels are known by those of skill in the art and include, but are not limited to, particles, fluorescent dyes, haptens, enzymes and their chromogenic, fluorogenic, and chemiluminescent substrates, and other labels that are described in the MOLECULAR PROBES HANDBOOK OF FLUORESCENT PROBES AND RESEARCH CHEMICALS by Richard P. Haugland, $6^{th}$ Ed., (1996), and its subsequent $7^{th}$ edition and $8^{th}$ edition updates issued on CD Rom in November 1999 and May 2001, respectively, the contents of which are incorporated by reference, and in other published sources.

"Monovalent antibody fragment" refers to an antibody fragment that has only one antigen-binding site. Examples of monovalent antibody fragments include, but are not limited to, Fab fragments (no hinge region), Fab' fragments (monovalent fragments that contain a heavy chain hinge region), and single-chain fragment variable (ScFv) proteins.

"Non-antibody immunoglobulin-binding protein" means a protein that binds selectively and noncovalently to a member of the Ig superfamily of proteins, including but not limited to proteins A, G, and L, hybrids thereof (A/G), recombinant versions and cloned versions thereof, fusions of these proteins with detectable protein labels, and lectins but the protein itself is not an antibody or an antibody fragment.

"Non-antibody immunoglobulin-binding peptide" means a peptide that selectively and noncovalently binds to a member of the Ig superfamily of proteins, such as a peptide that is selected by a process of screening against a biomolecular library.

"Peptide" means a polymer of amino acids, and includes polypeptides.

"Protein G" means proteins comprising one or more natural IgG-binding domains of protein G, hybrids of the natural IgG-binding domains, and mutants thereof wherein the variant retains the capability of binding IgG, or fragments thereof.

"Protein A" means proteins comprising one or more natural IgG-binding domains of protein A, hybrids of the natural IgG-binding domains, and mutants thereof wherein the variant retains the capability of binding IgG, or fragments thereof.

"Protein L" means proteins comprising one or more natural antibody light-chain-binding domains of protein L, hybrids of the natural antibody light-chain-binding domains, and mutants thereof wherein the variant retains the capability of binding antibody light chain, or fragments thereof.

"Selectively binds" refers to the situation in which one member of a specific intra or inter species binding pair will not show any significant binding to molecules other than its specific intra- or inter-species binding partner (e.g., an affinity of about 100-fold less), i.e. minimal cross-reactivity.

"Subcellular component" means functional units within a cell, including but not limited to, for example, membranes, organelles, receptors, nucleus, chromosomes, chloroplasts, peroxisomes, polyribosomes, mitochondria, lysosomes, DNA, RNA, endogenous proteins, peptides, enzymes, hormones, and factors.

"Target" means any entity to be detected by the association of the target-binding antibody with it.

II. Methods and Compositions

In accordance with the subject invention, methods and compositions are provided that facilitate the determination of a desired target in a biological sample. The method is performed in two steps. The immunolabeling complex, which contains the target-binding antibody and the labeling protein bound by a detectable label, is pre-formed followed by the addition to a sample suspected of containing the desired target. The labeling protein is either a monovalent Fab, fragment or a non-immunoglobulin peptide or protein, and specifically binds a selected region of the target-binding antibody. The labeling protein is covalently attached to one or more detectable labels, wherein the detectable labels can be the same or different allowing for multiparameter applications. After addition of the pre-formed immunolabeling complex to a sample, followed by sufficient time for the complex to bind with the target, detection of the label is determined. Methods of visualizing the label depend on the label attached to the labeling protein.

The labeling proteins bind selectively and with high affinity to a selected region of the target-binding antibody. These labeling proteins bind selectively to the same region of the target-binding antibody. The binding region for the labeling proteins may be a selected peptide linker (including the J region), light chain or heavy chain of the target-binding antibody; preferably the labeling protein binds the Fc region of the target-binding antibody. The target-binding antibody may be bound with one or more labeling proteins and the labeling proteins may be bound with one label, two similar labels, two distinct labels or multiple combinations thereof. Binding of more than one label, such as two different dyes on the same protein or on different proteins, used in different proportions, permits combinatorial applications that increase the number of detectable targets in the sample. Typically the same dye is used on a given labeling protein and the labeling proteins are monovalent Fab fragments or non-antibody peptide or proteins.

In this method, the labeling protein can be either an antibody fragment, such as, but not limited to, anti-Fc, an anti-Fc isotype, anti-J chain, anti-kappa light chain, anti-lambda light chain, or a single-chain fragment variable protein; or a non-antibody peptide or protein, such as, for example but not limited to, soluble Fc receptor, protein G, protein A, protein L, lectins, or a fragment thereof. Typically, the labeling protein is a Fab fragment specific to the Fc portion of the target-binding antibody or to an isotype of the Fc portion of the target-binding antibody. The monovalent Fab fragments are produced from either murine monoclonal antibodies or polyclonal antibodies generated in a variety of animals, for example but not limited to, rabbit or goat. These fragments can be generated from any isotype such as murine IgM, $IgG_1$, $IgG_{2a}$, $IgG_{2b}$ or $IgG_3$. Alternatively, a non-antibody protein or peptide such as protein G, or other suitable proteins, can be used alone or coupled with albumin wherein albumin is complexed with the detectable label. Preferred albumins of the invention include human and bovine serum albumins or ovalbumin.

Labels that are covalently attached to the labeling proteins are known by those of skill in the art and include, but are not limited to, radiolabels, pigments, dyes or other chromogens, spin labels, fluorescent compounds, haptens, electron transfer agents, and particles. The label can also be a precursor to a luminescent substance, a bioluminescent substance, a chemiluminescent substance, or a metal-containing substance. Preferred labels are fluorescent moieties such as those described in the MOLECULAR PROBES HANDBOOK OF FLUORESCENT PROBES AND RESEARCH CHEMICALS by R. P. Haugland $8^{th}$ Ed., CD-ROM (2001). Particullary preferred are xanthenes (e.g., fluoreceins, rhodamines and rhodols) especially sulfonated xanthenes such as those disclosed in U.S. Pat. No. 6,130,101 and UK 9611997.9 and fluorinated xanthenes such as those disclosed in U.S. Pat. No. 6,162,931; and coumarins, especially sulfonated coumarins such as those described in U.S. Pat. No. 5,969,157 and fluorinated coumarins such as those disclosed in U.S. Pat. No. 5,830,912; and cyanines especially sulfonated cyanines disclosed and PCT/01/30404 publication. Other preferred labels are fluorescent proteins, especially phycobiliprotein and tandem-dye conjugates thereof as well as haptens such as biotin including desthibiotin) and enzymes, described in greater detail below.

Preparation of labeling proteins using low molecular weight reactive dyes is known by those of skill in the art and is well documented, e.g., by Richard P. Haugland, MOLECULAR PROBES HANDBOOK OF FLUORESCENT PROBES AND RESEARCH CHEMICALS, Chapters 1-3 (1996) and by Brinkley, Bioconjugate Chem. 3, 2 (1992). Labeling proteins typically result from mixing appropriate reactive dyes and the protein to be conjugated in a suitable solvent in which both are soluble. The majority of the preferred dyes of the invention are readily soluble in aqueous solutions, facilitating conjugation reactions with most biological materials. For those reactive dyes that are photoactivated, conjugation requires illumination of the reaction mixture to activate the reactive dye.

A particular advantage of the current invention over other methods of labeling target-binding antibodies is that it provides for a novel method to directly label the antibodies in any solution containing primary amines or non-antibody proteins, for example from ascites fluid, hybridoma culture supernatant, serum, in the presence of stabilizing proteins like BSA, gelatin, ammonium ions, or buffers like TRIS. Consequently, the methods of the instant invention provide a means to rapidly screen hybridomas for antibody expression and quality of antibody properties (e.g. affinity, specificity, cross-reactivity, isotype, abundance).

In the methods described above, the labeling complexes, whether for single or multicolor detection systems, are combined with a sample thought to contain target materials in any way that facilitates contact between the immunolabeling complexes and the target of interest. Preferred targets of the invention are biological materials and include, for example, but not limited to, a cell, receptor, membrane, protein, nucleic acid, or carbohydrate, but can be any antigenic determinant.

Prior to combination with the immunolabeling complexes, the sample is prepared in a way that makes the target materials in the sample accessible to the immunolabeling complexes. Typically, the samples used in the invention are comprised of tissue, cells, cell extracts, cell homogenates, purified or reconstituted proteins, recombinant proteins, biological fluids, or synthesized proteins. Large macromolecules such as immunolabeling complexes tend to be impermeant to membranes of live biological cells. Treatments that permeabilize the plasma membrane, such as electroporation, shock treatments, or high extracellular ATP, can be used to introduce the labeling mixture and its immunolabeling complexes into cells. Alternatively, the labeling mixture and its immunolabeling complexes can be physically inserted into cells, e.g. by pressure microinjection, scrape loading, patch-clamp methods, or phagocytosis. However, the target materials may require purification or separation prior to addition of the immunolabelling complexes, which will depend on the way the antigenic determinants are contained in the sample. When the sample contains purified target materials, the purified target materials may still be mixtures of different materials. For example, purified protein or nucleic acid mixtures may contain several different proteins or nucleic acids. Alternatively, the purified target materials may be electrophoresed on gels such as agarose or polyacrylamide gels to provide individual species of target materials that may be subsequently blotted onto a polymeric membrane or detected within the gel matrix. Preparation of a sample containing purified nucleic acids or proteins generally includes denaturation and neutralization. DNA may be denatured by incubation with base (such as sodium hydroxide) or heat. RNA is also denatured by heating (for dot blots) or by electrophoresing in the presence of denaturants such as urea, glyoxal, or formaldehyde, rather than through exposure to base (for Northern blots). Proteins are denatured by heating in combination with incubation or electrophoresis in the presence of detergents such as sodium dodecyl sulfate. The nucleic acids are then neutralized by the addition of an acid (e.g., hydrochloric acid), chilling, or addition of buffer (e.g., Tris, phosphate or citrate buffer), as appropriate.

Preferably, the preparation of a sample containing purified target materials further comprises immobilization of the target materials on a solid or semi-solid support. Purified nucleic acids are generally spotted onto filter membranes such as nitrocellulose filters or nylon membranes in the presence of appropriate salts (such as sodium chloride or ammonium acetate) for DNA spot blots. Alternatively, the purified nucleic acids are transferred to nitrocellulose filters by capillary blotting or electroblotting under appropriate buffer conditions (for Northern or Southern blots). To permanently bind nucleic acids to the filter membranes, standard cross-linking techniques are used (for example, nitrocellulose filters are baked at 80° C. in vacuum; nylon membranes are subjected to illumination with 360 nm light). The filter membranes are then incubated with solutions designed to prevent nonspecific binding of the nucleic acid probe (such as BSA, casein hydrolysate, single-stranded nucleic acids from a species not related to the probe, etc.) and hybridized to probes in a similar solution. Purified proteins are generally spotted onto nitrocellulose or nylon filter membranes after heat and/or detergent denaturation. Alternatively, the purified proteins are transferred to filter membranes by capillary blotting or electroblotting under appropriate buffer conditions (for Western blots). Nonspecifically bound probe is washed from the filters with a solution such as saline-citrate or phosphate buffer. Filters are again blocked, to prevent nonspecific adherence of immunolabeling complexes. Finally, samples are mixed with immunolabeling complexes. Nonspecifically bound immunolabeling complexes are typically removed by washing.

When the sample contains cellular nucleic acids (such as chromosomal or plasmid-borne genes within cells, RNA or DNA viruses or mycoplasma infecting cells, or intracellular RNA) or proteins, preparation of the sample involves lysing or permeabilizing the cell, in addition to the denaturation and neutralization already described. Cells are lysed by exposure to agents such as detergent (for example sodium dodecyl sulfate, Tween, sarkosyl, or Triton), lysozyme, base (for example sodium, lithium, or potassium hydroxide), chloroform, or heat. Cells are permeabilized by conventional methods, such as by formaldehyde in buffer.

As with samples containing purified target materials, preparation of the sample containing cellular target materials typically further comprises immobilization of the target materials on a surface such as a solid or semi-solid support. The targets may be arrayed on the support in a regular pattern or randomly. These supports include such materials as slides, beads, optical fibers, and membranes. The beads are preferably fluorescent or nonfluorescent polystyrene, the slides and optical fibers are preferably glass or plastic, and the membrane is preferably poly(vinylidene difluoride) or nitrocellulose. Thus, for example, when the sample contains lysed cells, cells in suspension are spotted onto or filtered through nitrocellulose or nylon membranes, or colonies of cells are grown directly on membranes that are in contact with appropriate growth media, and the cellular components, such as proteins and nucleic acids, are permanently bound to filters as described above. Permeabilized cells are typically fixed on microscope slides with known techniques used for in situ hybridization and hybridization to chromosome "squashes" and "spreads," (e.g., with a reagent such as formaldehyde in a buffered solution). Alternatively, the samples used may be in a gel or solution.

Following the combining of the sample with the labeling mixture, unbound immunolabeling complexes that do not bind to the target are optionally removed from the sample by conventional methods, such as washing. The bound immunolabeling complex that binds to the target can be fixed in place with the usual fixatives (e.g. formaldehyde, glutaraldehyde) and fixation methods. Fixation can be utilized to improve the durability of the sample and to prevent transfer of the noncovalently complexed labeling protein to other targeting antibodies in the sample that have the same specific binding region.

Detection of the bound label is performed using methods and reagents well known to those skilled in the art. A preferred method of detection of the invention is through the use of fluorescence. Fluorescence from the immunolabeling complex binding to the target can be visualized with a variety of imaging techniques, including ordinary light or fluorescence microscopy, confocal laser-scanning microscopy, and flow cytometry, optionally using image deconvolution algorithms. Three-dimensional imaging resolution techniques in confocal microscopy utilize knowledge of the microscope's point spread function (image of a point source) to place out-of-focus light in its proper perspective. Multiple-labeled target materials are optionally resolved spatially, chronologically, by size, or using detectably different spectral characteristics (including excitation and emission maxima, fluorescence intensity, fluorescence lifetime, fluorescence polarization, fluorescence photobleaching rates, or combinations thereof), or by combinations of these attributes. Typically, multiple-labeled target materials are resolved using different labeling proteins with distinct spectral characteristics for each target material. Alternatively, the labels on the labeling proteins are the same but the samples are labeled and viewed sequentially or are spatially separated.

Additionally, enzymes can be used where there occurs an enzyme-dependent secondary generation of signal, such as the formation of a colored product from a non-colored substrate. Enzyme labels or enzyme labeling systems are desirable in that they can achieve signal amplification and greater distinctions from backgrounds. The enzyme breaks down a substrate to produce a chromophore or fluorophore or other detectable signal, thus amplifying the sensitivity of the assay and, if the substrate yields a distinct product at or near its site of formation, visualizing the site of the antigen/antibody complex in the sample. The substrate is selected to yield the preferred measurable product. Chromogenic, fluorogenic and chemiluminescence-generating enzyme substrates are preferred. These enzymes are enzymes for which substrates yielding useful chromophores, fluorophores, or chemiluminescence are known. Such substrates are extensively used in the art and are described the MOLECULAR PROBES HANDBOOK OF FLUORESCENT PROBES AND RESEARCH CHEMICALS by R. P. Haugland $6^{th}$ Ed., (1996) and its subsequent $7^{th}$ edition and $8^{th}$ edition updates issued on CD Rom in November 1999 and May 2001, respectively, the contents of which are incorporated by reference, and in other published sources.

Preferred enzyme substrates of the invention are enzyme substrates that yield a fluorescent product that localizes at or near the site of enzyme activity. Enzymes of use in the method include any enzymes that utilize a chromogenic, fluorogenic, or chemiluminescence-generating substrate. Preferred enzymes of the invention include peroxidases, phosphatases, glycosidases, aequorins, or luciferases, and more specifically, HRP, *Coprinus cinereus* peroxidase, *Arthromyces ramosus* peroxidase, alkaline phosphatase, β-galactosidase, β-glucuronidase, or a protein A or protein G fusion protein of luciferase.

A preferred chromogenic (and in some cases fluorogenic) substrate and enzyme combination uses oxidoreductases such as horseradish peroxidase, *Coprinus cinereus* peroxidase, or *Arthromyces ramosus* peroxidase and a substrate such as 3,3'-diaminobenzidine (DAB) or 3-amino-9-ethylcarbazole (AEC), which yield a distinguishing color (brown and red, respectively). Other chromogenic oxidoreductase substrates that yield detectable products include, but are not limited to: 2,2'-azino-bis(3-ethylbenzthiazoline-6-sulfonic acid (ABTS), o-phenylenediamine (OPD), 3,3',5,5'-tetramethylbenzidine (TMB), o-dianisidine, 5-aminosalicylic acid, and 4-chloro-1-naphthol. Fluorogenic substrates include, but are not limited to, homovanillic acid or 4-hydroxy-3-methoxyphenylacetic acid, reduced phenoxazines and reduced benzothiazines, including the Amplex Red reagent and its variants (Miike, U.S. Pat. No. 4,384,042), reduced dihydroxanthenes, including the Amplex Gold reagent and other dihydrofluoresceins such as those described in U.S. Pat. No. 6,162,931, and dihydrorhodamines such as dihydrorhodamine 123. Peroxidase substrates that are tyramides, as described in U.S. Pat. Nos. 5,196,306; 5,583,001 and 5,731, 158, which are incorporated by reference, represent a unique class of peroxidase substrates in that they can be intrinsically detectable before action of the enzyme but are "fixed in place" by the action of a peroxidase in the process termed tyramide signal amplification (TSA). These substrates, which are a preferred embodiment of the instant invention, are extensively utilized to label targets in samples that are cells, tissues, or arrays for their subsequent detection by microscopy, flow cytometry, optical scanning, and fluorometry.

Another preferred chromogenic (and in some cases fluorogenic) substrate and enzyme combination uses a phosphatase enzyme such as calf intestinal alkaline phosphatase, an acid phosphatase, or a recombinant version of such a phosphatase in combination with a chromogenic substrate such as 5-bromo-4-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, carboxyumbelliferyl phosphate, 6,8-difluoro-7-hydroxy4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39, or related phosphates (U.S. Pat. Nos. 5,316,906 and 5,443,986).

Glycosidases, in particularly β-galactosidase, β-glucuronidase, and β-glucosidase, are additional suitable enzymes. Appropriate chromogenic substrates include, but are not limited to, 5-bromo-4-chloro-3-indolyl β-D-galactopyranoside (X-gal) and similar indolyl galactosides, glucosides, and glucuronides, o-nitrophenyl β-D-galactopyranoside (ONPG), and p-nitrophenyl β-D-galactopyranoside. Preferred fluorogenic glycosidase substrates include resorufin β-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl β-D-galactopyranoside, carboxyumbelliferyl β-D-galactopyranoside, and fluorinated coumarin β-D-galactopyranosides (U.S. Pat. No. 5,830,912).

Additional enzymes include, but are not limited to, hydrolases such as cholinesterases and peptidases, oxidases such as glucose oxidase and cytochrome oxidases, and reductases, for which suitable substrates are known.

Enzymes and their appropriate substrates that produce chemiluminescence are preferred for some assays. These include, but are not limited to, natural and recombinant forms of luciferases and aequorins and include their chimeras with proteins that include protein A, protein G, and protein L. Chemiluminescence-producing substrates for phosphatases, glycosidases, and oxidases such as those containing stable dioxetanes, luminol, isoluminol, and acridinium esters are additionally useful.

When using florescent dyes to detect the desired target the sample is illuminated at a suitable absorption wavelength. A suitable wavelength is one that comes within the range of absorption wavelengths for each of the fluorescent dyes being used. Typically, the mixture is illuminated by a light source capable of producing light at or near the wavelength of maximum absorption of the dye or dyes, such as by ultraviolet or visible lamp, an arc lamp, a laser, or even sunlight. Illumination of the sample at a suitable wavelength results in one or more illuminated targets that are then analyzed according to the response of their fluorescence to the illumination. The illuminated targets are observed with any of a number of means for detecting a fluorescent response emitted from the illuminated target, including but not limited to visual inspection, cameras and film or other imaging equipment, or use of instrumentation such as fluorometers, plate readers, laser-based scanners, microscopes, or flow cytometers, or by means for amplifying the signal such as a photomultiplier (PMT).

In a particular aspect of the detection method, the labeling mixture is combined with a sample of cells in a fluid, such as ascites, hybridoma supernatant, or serum, and the presence or absence of the target in such cells is detected by using an automated instrument that sorts cells according to the detectable fluorescence response of the detectable moieties in the immunolabeling complexes bound to such cells, such as by fluorescence activated cell sorting (FACS), which is described in Mansour, et al., U.S. Pat. No. 4,665,024 (1987) and is incorporated by reference. In another aspect of the invention, additional detection reagents are combined with the sample concurrently with or following the labeling mixture. Such additional detection reagents include, but are not limited to reagents that selectively detect cells or subcellular components, ions, or indicate the cell viability, life cycle, or proliferation state. For example, the additional detection reagent is a labeled antibody that is directly or indirectly detectable and another additional detection reagent is a stain for nucleic acids, for F-actin, or for a cellular organelle.

While there are many applications in the field of immunological monitoring in which the presence of body fluid antibodies and antigens are detected by a variety of methods, these methods usually measure one antibody or antigen at a time and tend to be time consuming and costly. One of the strengths of the methods of the instant invention is the ability to simultaneously, but discretely, analyze multiple targets, especially wherein multiple antibodies from the same species (e.g. mouse monoclonal antibodies) are utilized. Another strength is the ability to rapidly prepare and optimize the complexes and to mix and combine colors of products for detection of the multiple targets in a sample. Determination of more than one target in a sample is accomplished with a labeling mixture containing more than one immunolabeling complex wherein a first target-binding antibody is bound to a labeling proteins with a first label and a second target-binding protein is bound to a labeling protein with a second label, wherein the first and second labels are detectably distinct. Thus multiple, distinct targets, can be determined simultaneously. Alternatively, any combination of labels, labeling proteins and target-binding antibodies may be used allowing for unlimited options.

In accordance with the subject invention compositions of the present invention include isolated immunolabeling complexes and isolated monovalent labeling proteins. The labeling protein is labeled with one or more labels. Typically, the labels that are attached to the labeling protein are directly detectable moieties, which directly detectable moieties are optionally the same or different, or the label is an enzyme or a hapten that is indirectly detectable. In a preferred embodiment of the invention the labeling protein is prepared by the process of (a) complexation of the unlabeled labeling protein with an immobilized form of its complementary binding protein; and (b) chemical conjugation of the labeling protein to the label; and (c) disaggregation of the covalently labeled labeling protein from the immobilized complementary protein.

Covalent conjugates of the enzyme and the labeling protein of the invention that are suitable for preparation of labeling complexes are typically prepared by methods well known in the art (MOLECULAR PROBES HANDBOOK OF FLUORESCENT PROBES AND RESEARCH CHEMICALS, Chapter 5 (1996)). Additionally, fusion proteins of enzymes such as of alkaline phosphatase, horseradish peroxidase, luciferase, and aequorin with the labeling proteins, protein A and protein G, have been described (Sun et al., J. Immunol. Meth. 152, 43 (1992); Eliasson et al., J. Biol. Chem. 263, 4323 (1988); Eliasson et al., J. Immunol. 142, 575 (1989)); U.S. Pat. No. 5,766,941 and 5,798,441; U.S. Pat. No. 5,292, 658 and 5,418,155) that can be directly complexed with the target-binding antibody. Fusion proteins of green-fluorescent protein (GFP) and its wavelength-shifted analogs with certain immunoglobulin-binding proteins provide labeling proteins with a well-defined stoichiometry and structure. Labeling proteins that are conjugates of phycobiliproteins (e.g. U.S. Pat. Nos. 4,520,110; 4,859,582; 5,055,556; all incorporated by reference) or of tandem conjugates of phycobiliproteins with additional dyes (e.g. U.S. Pat. No. 4, 542,104; incorporated by reference) are prepared by similar coupling methods.

Chemical labeling of the monovalent antibody fragment is optionally performed while the antibody fragment is immobilized on a matrix, such as while bound to its complementary binding site. For example, an Fab fragment of goat anti-(mouse Fc) or a protein A or protein G can be bound to a whole mouse IgG that has been immobilized on agarose. Following reaction with a reactive dye, or coupling to a protein such as a phycobiliprotein, a tandem conjugate of a phycobiliprotein with an Alexa Fluor dye (Molecular Probes, Inc.) or with an enzyme by standard methods, the excess reactive dye is removed while the monovalent labeling protein is still immobilized and then the labeled monovalent antibody is eluted by reducing the pH. This method has the simultaneous advantages of facilitating elimination of the unconjugated reactive dye and protecting the combining region of the monovalent antibody. Furthermore, we have observed that fluorescent dye conjugates prepared by this indirect method typically have greater fluorescence or activity than do conjugates of the monovalent labeling protein prepared using the same reactive dye in a homogeneous solution. We have also observed that less labeled monovalent labeling protein is required to achieve the same or superior detectability when preparing a labeling complex with the target-binding antibody. Alternatively, smaller quantities of target-binding antibody can be used when pre-forming the immunolabeling complexes to achieve the same detectablity. Optionally, the target-binding antibody is about 5 micrograms to about 0.001 micrograms.

The invention also includes an isolated protein G complex consisting essentially of protein G and a non-covalently bound albumin. The albumin is covalently labeled with one or more detectable labels, as described above, where the detectable labels are optionally the same or different. Various types of albumin can be used including, for example, human albumin, bovine serum albumin, or ovalbumin.

In yet another aspect of the invention, the isolated immunolabeling complex is made by combining, in vitro, one or more target-binding antibodies with an excess of labeling protein that has been covalently labeled as described above, under conditions suitable for the labeling protein to bind selectively and with high affinity to a selected region of said target-binding antibody to form an immunolabeling complex, and isolating said immunolabeling complex. In one example of forming the complex, combining means mixing a solution of the isolated covalently labeled labeling protein with a solution of the target-binding antibody in a suitable buffer for a period sufficient to form a noncovalent complex. Typically this period is under five minutes but may be less than one minute.

When preparing the immunolabeling complex, stock solutions of both the labeling protein and the target-binding antibody are typically near 1 mg/mL in an appropriate buffer, although more or less concentrated solutions are also suitable. Generally, the labeling protein is mixed in a molar ratio of at least one to 50 moles of labeling protein to one mole of the region of the target-binding antibody to be complexed. More commonly a ratio of at least one to as many as 10 moles of labeling protein per mole of target-binding antibody is combined. With an Fab fragment of an antibody to the Fc region of a target-binding antibody, a molar ratio of approximately 2 to 10 is typical, more typically 3 to 5 (particularly for complexes in which the labeling protein has been labeled while immobilized on an affinity matrix). The ease of formation of the complex permits rapid optimization of the complex and assessment of the effect of variation in experimental parameters. A particularly unique advantage of the invention is that the stoichiometry of the complex is easily adjusted to provide complexes with different ratios of labeling protein to target-binding antibody, and thus there is some control over the ultimate detectability of the target in the sample. This feature is impractical with primary antibodies that have been directly chemically labeled with dyes. Complexes that have been labeled with the same dye but at different molar ratios can be separately detected by the differences in their intensities.

Complex formation appears to occur almost within the mixing time of the solutions (<1 minute) but the reaction typically is allowed to proceed for at least 5 minutes and can be longer before combining the antibody complex with the sample. Although complex formation can be reversed by addition of an unlabeled antibody that contains the same binding region, reversibility is very slow; furthermore, following staining of the sample with the complex, the sample can be "fixed" using aldehyde-based fixatives by methods that are commonly practiced by those skilled in the art of immunolabeling.

A unique and important advantage of the method of the invention is the ability to form the immunolabeling complex from exceedingly small quantities of the target-binding antibody and labeling protein, which is impractical when using chemically reactive dyes. Complexes of the invention have been prepared from sub-micrograms of a target-binding antibody with sub-micrograms of a labeling protein. The process of forming a labeling complex can easily be automated. An important use of this characteristic is that of screening hybridoma supernatants in the generation and optimization of new antibodies, where the very small quantity of antibody present in a single well makes it impractical to perform chemical labeling.

In one aspect of the invention, a capture component is added to the labeling mixture, prior to combining the labeling mixture with the sample, to remove excess labeling protein. For applications in which immunolabeling complexes of multiple primary antibodies from the same species (e.g. mouse monoclonal antibodies) or cross-reacting species (e.g. mouse and human antibodies) are to be used simultaneously or sequentially, it is necessary to quench or otherwise remove any excess labeling protein by use of a capture component or by other means to avoid inappropriate labeling of the sample. The most effective capturing components to capture excess labeling protein are those that contain the binding site of the labeling protein but are themselves not labeled, preferably an antibody or antibody fragment. Capture components may be free in solution or immobilized on a solid phase, such as agarose, cellulose, or a natural or synthetic polymer, to facilitate separation of the excess capture component from the labeled protein. The capture component is optionally attached to a microsphere or magnetic particle. Any of the isolated labeling mixtures optionally include a capture component to remove excess labeling protein. However, separation of excess labeling protein is not essential for successful utilization of the invention, particularly when using a single target-binding antibody.

Included in the invention are isolated labeling mixtures comprising one or more immunolabeling complexes, wherein at least one immunolabeling complex is comprised of a target-binding antibody, is selective for a target in a sample, and a labeling protein, as described above, that binds selectively and with high affinity to a selected region of the target-binding antibody. More preferably the labeling mixture contains at least three such complexes. The potential number of immunolabeling complexes that can be used simultaneously is principally limited by the number of targets for which selective antibodies are available and the ability to spatially or spectrally resolve the detectable signals, such as on a Western blot, a protein array, a chromosome "spread", or a microsphere or "chip" array (e.g., U.S. Pat. Nos. 5,981,180 and 5,736,330).

These labeling mixtures optionally include additional detection reagents such as those known to those skilled in the art, including reagents that localize the same or additional targets in the sample. Preferred additional detection reagents include stains for cell organelles, reagents to indicate the state of cell viability or proliferation, and enzyme substrates. Other preferred additional detection reagents are additional antibodies that can be detected in conjunction with direct or indirect labeling methods, wherein the targets of such additional antibodies and of the target-binding antibody are optionally the same or different.

In one aspect of the invention, the labeling protein is a monovalent fragment that is made by (a) generating a labeling antibody against an antigen, where said antigen is a Fc region of one or more isotypes of an antibody from a different species; (b) digesting said labeling antibody to generate multiple monovalent fragments; (c) covalently labeling said monovalent fragments with one or more labels; and (d) isolating the labeled fragments.

Particularly preferred for use with mouse or rat monoclonal antibodies is an Fab fragment of an antibody to mouse Fc, wherein the whole antibody was produced in goat, chicken or other species. Preferred as a labeling protein for complexing with either targeting or secondary antibodies produced in other species (e.g. rabbit, sheep, goat, donkey, bovine, horse, guinea pig, chicken) are antibodies to the Fc region of these target-binding or secondary antibodies produced in a non-cross-reacting animal, in particular Fab fragments of such antibodies. Particularly where the primary antibody to be labeled is a mouse, rat, or human antibody, additional selectivity can be obtained by utilizing an antibody directed at a particular isotype of the primary antibody, such as toward $IgG_1$, $IgG_{2a}$, or $IgG_3$ isotypes.

The target-binding antibody is selected based on the desired target, where the target is an antigen selected for investigation or analysis. The chemical identity of the target antigen may be known or unknown. The target is optionally a material of biological or synthetic origin that is present as a molecule or as a group of molecules. Typically, the target is a biological material or antigenic determinant. Biological materials include, but are not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatized nucleic acids (including deoxyribo- and ribonucleic acids and peptide nucleic acids), DNA and RNA fragments and derivatized fragments (including single and multi-stranded fragments), natural and synthetic drugs, receptors, virus particles, bacterial particles, virus components, biological cells, cellular components (including cellular membranes and organelles), natural and synthetic lipid vesicles, and polymer membranes. Typically the target material is present as a component or contaminant of a sample taken from a biological or environmental system.

III. Kits

Suitable kits for preparing a labeling protein, for preparing an immunolabeling complex, and for immunolabeling a target in a sample also form part of the invention. Such kits can be prepared from readily available materials and reagents and can come in a variety of embodiments. The contents of the kit will depend on the design of the assay protocol or reagent for detection or measurement. Generally, the kits will contain instructions, appropriate reagents and labels, and solid supports, as needed. Typically, instructions include a tangible expression describing the reagent concentration or at least one assay method parameter such as the relative amounts of reagent and sample to be admixed, maintenance time periods for reagent/sample admixtures, temperature, buffer conditions and the like to allow the user to carry out any one of the methods or preparations described above. Where a kit is designed for a simple detection assay for a target using a single highly specific antibody, the kit contains this highly specific antibody pre-complexed with a labeling protein. Alternatively, the kit comprises panels of antibodies each pre-complexed with a unique labeling protein whose recognition pattern for the desired target is calibrated or the kit comprises panels of antibodies and a separate labeling protein or labeling proteins. A labeled competitive mimotope or mixture is optionally additionally included to permit the assays to be conducted by competition of the unlabeled target in the sample with the labeled mimotope.

A kit for preparation of optimal labeling proteins typically comprises (a) a monovalent antibody fragment that binds to a specific region of a target-binding antibody, (b) a chemically reactive dye, and (c) an immobilization matrix comprising the specific region of the target-binding antibody to which the monovalent antibody fragment binds.

In one embodiment of the invention, the kit comprises (a) a mixture of one or more monovalent antibody fragments that bind to a specific region of one or more antibody isotypes, where each fragment is covalently labeled with one or more labels, (b) a capture component to which the antibody fragments bind, and optionally (c) comprises one or more target-binding antibodies. Preferably the capture component is purified mouse IgG or serum from a non-immune mouse and the label is a fluorescent molecule. In another preferred embodiment of this kit, the antibody fragment is an antibody to the Fc region of the target-binding antibody that is matched to or cross-reacts with the species from which the target-binding antibody is derived. In a further preferred embodiment of the kit, the labeled monovalent antibody fragment has been labeled while immobilized on an affinity matrix.

In another embodiment, a kit is provided for preparing an immunolabeling complex comprising another version of the kit for preparing (a) an immunolabeling complex that comprises a protein G complexed with a labeled albumin and (b) a capture component to which the protein G complexed with albumin binds. In a more particular embodiment of this kit, the capture component is purified mouse IgG or non-immune mouse serum and the albumin is human albumin, bovine serum albumin, or ovalbumin. In a more preferred embodiment the albumin is ovalbumin.

Another kit of the invention that is useful for immunolabeling a target in a sample comprises a labeling mixture that contains one or more of the immunolabeling complexes as defined above and a buffer. In a more preferred embodiment, the kit contains three or more such immunolabeling complexes.

Yet another kit of the invention that is useful for immunolabeling a target in a sample comprises a labeling mixture that contains one or more of the immunolabeling complexes, as defined above, a buffer, and additional labeling reagents that optionally include (a) directly conjugated target-binding antibodies that may be the same or different, (b) stains for characterization of cellular organelles, cell viability, or cell proliferation state, or (c) enzyme substrates.

A wide variety of kits and components can be prepared according to the present invention, depending upon the intended user of the kit and the particular needs of the user.

IV. Applications

The instant invention has useful applications in basic research, high-throughput screening, immunohistochemistry, fluorescence in situ hybridization (FISH), microarray technology, diagnostics, and medical therapeutics. The invention can be used in a variety of assay formats for diagnostic applications in the disciplines of microbiology, immunology, hematology and blood transfusion, tissue pathology, forensic pathology, and veterinary pathology. The invention is particularly useful in the characterization and selection of optimized antibodies from hybridoma supernatants. Additionally, the invention can be used to deliver therapeutics to a specific target. In general, the current invention provides a versatile and convenient method to enhance any assay that uses an antibody as part of its detection methodology.

The instant invention can be used to study biological phenomena, such as, for example, cell proliferation, signal transduction in cells, or apoptosis. For illustration purposes only and not limitation, one could study thymidine analog 5-bromo-2'-deoxyuridine (BrdU) incorporation. BrdU is a marker for both cell proliferation and apoptosis, as it is readily incorporated into newly synthesized DNA that has progressed through the S-phase of the cell cycle and also into DNA break sites by deoxynucleotidyl transferase (TdT). Anti-BrdU antibodies are used to detect cells marked by BrdU incorporation. By being able to directly label the anti-BrdU antibodies, the current invention provides a convenient method to allow for detection of the incorporated BrdU by conventional immunohistochemistry or fluorescence, depending on detection method required.

Additionally, the current invention has the advantage of allowing staining for multiple targets in one cocktail, thereby reducing the need for more samples or processing steps per experiment. This is particularly important when analyzing precious samples (e.g., pediatric samples, leukocytes isolated from biopsies, rare antigen-specific lymphocytes and mouse tissues that yield a small number of cells). Although it is currently possible to simultaneously measure up to 11 distinct fluorescent colors through a convoluted series of novel developments in flow cytometry hardware, software, and dye chemistry, the use of these advances has been severely limited by the lack of commercial availability of spectrally distinct directly labeled primary and secondary antibodies. Although labeled secondary antibodies directed at individual isotype-specific targeting antibodies (e.g., anti-$IgG_1$ isotype antibodies) exist, it is not possible to use this type of labeled antibody to detect more than one of the same isotype of an antibody (e.g., an $IgG_1$ isotype antibody) in a single sample due to cross-reactivity. The current invention overcomes these limitations by providing for a convenient and extremely versatile method of rapidly labeling either small or large quantities of any primary antibody including primary antibodies of the same isotype to be used in, for example, multicolor flow cytometry and on Western blots. This advance in multicolor systems has a number of advantages over current two- and three-color flow cytometric measurements. For example, no combination of one-color stains can accurately enumerate or be used to isolate $CD3^+$ $CD4^+$ $CD8^-$ T cells (excluding, for example $CD3^+$ $CD4^+$ $CD8^+$ T cells and small $CD4^+$ monocytes). The use of cell membrane markers to study leukocyte composition in blood and tissue serves as an example of an analytical monoclonal antibody application, particularly in combination with flow cytometry. It is also the example most relevant to studies of the immune system, because the cellular composition of blood and lymphoid tissue provides a 'window', allowing the analysis and monitoring of the immune system.

The methods of the invention can also be used in immunofluorescence histochemistry. Immunofluorescence histochemistry involves the use of antibodies labeled with fluorophores to detect substances within a specimen. The pathologist derives a great deal of information of diagnostic value by examining thin sections of tissue in the microscope. Tissue pathology is particularly relevant to, for example, the early diagnosis of cancer or premalignant states, and to the assessment of immunologically mediated disorders, including inflammation and transplant rejection. The problems associated with immunofluorescence histochemistry, however, stem from the limitations of the methods currently available for use in such application. For example, directly labeling an antibody can result in antibody inactivation and requires a relatively large of amount of antibody and time to do the conjugation. It is also expensive and impractical to prepare directly labeled antibodies having variable degrees of label substitution. Similarly, indirect labeling of an antibody has problems, such as lack of secondary antibody specificity, and reliance upon primary antibody differences, including antibody isotypes and available fluorophores, to do multicolor labeling. Secondary antibody labeling is not practical where the primary antibody is from the same species or of the same isotypes. Combinations of fluorophores or other detectable labels on the same target-binding antibody, which can be readily prepared in multiple mixtures by the methods on this invention, greatly increase the number of distinguishable signals in multicolor protocols. Lack of secondary antibody specificity arises when the specimen containing the targeted moiety and target-binding antibody are from homologous species. For example, BrdU-labeled DNA in rodent tissue is detected by immunohistochemical staining. The target-binding antibody is conventionally mouse anti-BrdU, and the detecting antibody system uses an anti-mouse immunoglobulin antibody, labeled with fluorescein. Because there is homology between mouse immunoglobulin and immunoglobulins from a number of rodent species (for example, rats, mice, hamsters, etc.), the detecting antibody not only binds to the target-binding antibody, but also nonspecifically binds to immunoglobulin in the tissue. The current invention eliminates this problem by pre-forming the immunolabeling complex and allows for a simple, rapid and convenient method to proceed with labeling with two, three or more fluorescent antibodies in one experiment. Very significantly, it can always be used with primary antibodies of either the same or different isotype, and always on tissue of the same or similar species as the primary antibody.

The instant invention also has application in the field of microarrays. Microarray technology is a powerful platform for biological exploration (Schena (Ed.), Microarray Biochip Technology, (2000)). Many current applications of arrays, also known as "biochips," can be used in functional genomics as scientists seek characteristic patterns of gene expression in different physiopathological states or tissues. A common method used in gene and protein microarray technology involves the use of biotin, digoxigenin (DIG), or dinitrophenyl (DNP) as an epitope or a "tag" such as an oligohistidine, glutathione transferase, hemagglutinin (HA), or c-myc. In this case a detectably labeled anti-biotin, anti-DIG, anti-DNP, anti-oligohistidine, anti-glutathione transferase, anti-HA, or anti-c-myc is used as the detection reagent. The instant invention allows for the use of multiple fluorophore- or enzyme-labeled antibodies, thereby greatly expanding the detection modalities and also providing for enhanced multiplexing and two-dimensional analysis capabilities.

Similarly, the invention can be used with protein microarrays and on Western blots. Protein microarrays can provide a practical means to characterize patterns of variation in hundreds of thousands of different proteins in clinical or research applications. Antibody arrays have been successfully employed that used a set of 115 antibody/antigen pairs for detection and quantitation of multiple proteins in complex mixtures (Haab et al., Genome Biology, 2, 4.1 (2001)). However, protein microarrays use very low sample volumes, which historically have significantly limited the use of antibody technology for this application. The invention of the application readily overcomes this limitation and provides a means to label antibodies with the fluorescent dyes using a very low sample volume and to automate formation of the staining complex and the staining process.

The present invention also provides a means for the specific detection, monitoring, and/or treatment of disease and contemplates the use of immunolabeling complexes to detect the presence of particular targets in vitro. In such immunoassays, the sample may be utilized in liquid phase, in a gel, or bound to a solid-phase carrier, such as an array of fluorophore-labeled microspheres (e.g., U.S. Pat. No. 5,981,180 and 5,736,330). For example, a sample can be attached to a polymer, such as aminodextran, in order to link the sample to an insoluble support such as a polymer-coated bead, plate, or tube. For instance, but not as a limitation, using the methods of the present invention in an in vitro assay, antibodies that specifically recognize an antigen of a particular disease are used to determine the presence and amounts of this antigen.

Likewise, the immunolabeling complexes of the present invention can be used to detect the presence of a particular target in tissue sections prepared from a histological specimen. Preferably, the tissue to be assayed will be obtained by surgical procedures, e.g., biopsy. The excised tissue will be assayed by procedures generally known in the art, e.g. immunohistochemistry, for the presence of a desired target that is recognized by an immunolabeling complex, as described above. The tissue may be fixed or frozen to permit histological sectioning. The immunolabeling complex may be labeled, for example with a dye or fluorescent label, chemical, heavy metal or radioactive marker to permit the detection and localization of the target-binding antibody in the assayed tissue. In situ detection can be accomplished by applying a detectable immunolabeling complex to the tissue sections. In situ detection can be used to determine the presence of a particular target and to determine the distribution of the target in the examined tissue: General techniques of in situ detection are well known to those of ordinary skill. See, for example, Ponder, "Cell Marking Techniques and Their Application," in MAMMALIAN DEVELOPMENT: A PRACTICAL APPROACH, Monk (ed.), 115 (1987).

For diagnosing and classifying disease types, tissues are probed with an immunolabeling complex, as defined above, that comprises a target-binding antibody to a target antigen associated with the disease, e.g., by immunohistochemical methods. Where the disease antigen is present in body fluids, such immunolabeling complexes comprising a target-binding antibody to the disease antigen are preferably used in immunoassays to detect a secreted disease antigen target.

Detection can be by a variety of methods including, for example, but not limited to, flow cytometry and diagnostic imaging. When using flow cytometry for the detection method, the use of microspheres, beads, or other particles as solid supports for antigen-antibody reactions in order to detect antigens or antibodies in serum and other body fluids is particularly attractive. Flow cytometers have the capacity to detect particle size and light scattering differences and are highly sensitive fluorescence detectors. Microfluidic devices provide a means to perform flow-based analyses on very small samples.

Alternatively, one can use diagnostic imaging. The method of diagnostic imaging with radiolabeled antibodies is well known. See, for example, Srivastava (ed.), RADIOLABELED MONOCLONAL ANTIBODIES FOR IMAGING AND THERAPY, Plenum Press (1988); Chase, "Medical Applications of Radioisotopes," in REMINGTON'S PHARMACEUTICAL SCIENCES, 18th Edition, Gennaro et al. (eds.) Mack Publishing Co., 624 (1990); and Brown, "Clinical Use of Monoclonal Antibodies," in BIOTECHNOLOGY AND PHARMACY, Pezzuto et al. (eds.), Chapman & Hall, 227 (1993). This technique, also known as immunoscintigraphy, uses a gamma camera to detect the location of gamma-emitting radioisotopes conjugated to antibodies. Diagnostic imaging is used, in particular, to diagnose cardiovascular disease and infectious disease.

Thus, the present invention contemplates the use of immunolabeling complexes to diagnose cardiovascular disease. For example, immunolabeling complexes comprising anti-myosin antibodies can be used for imaging myocardial necrosis associated with acute myocardial infarction. Immunolabeling complexes comprising antibodies that bind platelets and fibrin can be used for imaging deep-vein thrombosis. Moreover, immunolabeling complexes comprising antibodies that bind to activated platelets can be used for imaging atherosclerotic plaque and immunolabeling complexes.

Immunolabeling complexes of the present invention also can be used in the diagnosis of infectious diseases. For example, immunolabeling complexes comprising antibodies that bind specific bacterial antigens can be used to localize abscesses. In addition, immunolabeling complexes comprising antibodies that bind granulocytes and inflammatory leukocytes can be used to localize sites of bacterial infection. Similarly, the immunolabeling complexes of the present invention can be used to detect signal transduction in cells, the products of signal transduction, and defects, inhibitors, and activators of signal transduction.

Numerous studies have evaluated the use of antibodies for scintigraphic detection of cancer. Investigations have covered the major types of solid tumors such as melanoma, colorectal carcinoma, ovarian carcinoma, breast carcinoma, sarcoma, and lung carcinoma. Thus, the present invention contemplates the detection of cancer using immunolabeling complexes comprising antibodies that bind tumor markers (targets) to detect cancer. Examples of such tumor markers include carcinoembryonic antigen, α-fetoprotein, oncogene products, tumor-associated cell surface antigens, and necrosis-associated intracellular antigens. In addition to diagnosis, antibody imaging can be used to monitor therapeutic responses, detect recurrences of a disease, and guide subsequent clinical decisions and surgical procedures. In vivo diagnostic imaging using fluorescent complexes that absorb and emit light in the near infrared (such as those of the Alexa Fluor 700 and Alexa Fluor 750 dyes) is also known.

In addition to use in diagnostic applications, the invention contemplates the use of immunolabeling complexes as therapeutics. Immunolabeling complexes that are therapeutically substituted or therapeutic immunolabeling complexes, wherein the labeling protein is alternatively conjugated with a radioactive moiety, a toxin, or a drug, as opposed to with a detectable label, to form a drug-labeled protein or immunoconjugate, can be used to treat viral and bacterial infectious diseases, cardiovascular disease, autoimmune disease, and cancer. The objective of such therapy is to deliver cytotoxic doses of radioactivity, toxin, or drug to target cells, while minimizing exposure to non-target tissues.

Therapeutic agents useful in the treatment of a disease may be conjugated to the protein by methods known to those of skill in the art. Examples of such therapeutic agents include peptides; proteins; small organic drugs, such as, doxorubicin, daunorubicin, methotrexate, melphalin, chlorambucil, vinca alkaloids, 5-fluorouridine, and mitomycin-C; radioisotopes, such as, $^{131}$I, $^{67}$Cu, or $^{90}$Y; and cytotoxic agents, such as ricin, abrin, pokeweed antiviral protein, gelonin, diphtherin toxin, and *Pseudomonas endotoxin*. $^{131}$I can be covalently bound to the protein by methods known in the art, e.g., Iodogen reactions (Frank et al., Biochem. Biophys. Res. Commun. 80, 849 (1978)). $^{67}$Cu, one of the more promising radioisotopes for radioimmunotherapy due to its 61.5 hour half-life and abundant supply of beta particles and gamma rays, can be conjugated to the protein using the chelating agent, 6-(p-bromoacetamidobenzyl)-1,4,8,1 1-tetraazacyclotetradecane-N,N',N", N"'-tetraacetic acid (TETA). Alternatively, $^{90}$Y, which emits an energetic beta particle, can be coupled to a labeling protein using diethylenetriaminepentaacetic acid (DTPA), or more preferably, 1,4,7,10-tetraazacyclododecane-N,N',N",N"'-tetraacetic acid (DOTA) (Camera et al., J. Nucl. Med. 35, 882 (1994)). Agents such as glutaraldehyde or a carbodimide may conjugate the toxins to the protein. Small organic drugs, peptides, and proteins can be conjugated by various means known in the art, for example, but not limitation, through amide bonds and or linkers.

Administration of the therapeutically substituted immunolabeling complex may be by various means known in the art, but generally will be by injection, intravenous, intraarterial, intraperitoneal, intramuscular, subcutaneous, intrapleural, intrathecal, by perfusion through a regional catheter, or by direct intralesional injection. When administering therapeutic immunolabeling complexes by injection, the administration may be by continuous infusion, or by single or multiple boluses.

The therapeutic immunolabeling complex of the present invention can be formulated according to known methods to prepare pharmaceutically useful compositions, whereby the therapeutic immunolabeling complexes are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well known to those in the art. See, for example, REMINGTON'S PHARMACEUTICAL SCIENCES, 18th Ed. (1990).

For purposes of immunotherapy, a substituted immunolabeling complex and a pharmaceutically acceptable carrier are administered to a patient in a therapeutically effective amount. A combination of an immunolabeling complex and a pharmaceutically acceptable carrier is said to be administered in a "therapeutically effective amount" if the amount administered is physiologically significant. An agent is physiologically significant if its presence results in a detectable change in the physiology of a recipient patient. A useful therapeutic dose will vary with the particular therapeutic agent used, the particular disease type and history, and the specific considerations of the patient to be treated, such as the patient's age, weight, height, sex, general medical condition, and previous medical history. A physician administering the agent will know to calculate the effective therapeutic dose, which dose will be effective in reducing or eliminating the disease without compromising significantly normal tissues or cells of the patient. Typically, however, it is desirable to provide the recipient with a dosage of the substituted immunolabeling complex that is in the range of from about 1 pg/kg to 10 mg/kg (amount of agent/body weight of patient), although a lower or higher dosage may also be administered. For example, many studies have demonstrated successful treatment with doses of 0.1 to 1.0 milligram, while other studies have shown improved localization with doses in excess of 10 milligrams.

Additional pharmaceutical methods may be employed to control the duration of action of a substituted immunolabeling complex in a therapeutic application. Controlled release preparations can be prepared through the use of polymers to complex or adsorb a substituted immunolabeling complex. For example, biocompatible polymers include matrices of poly(ethylene-co-vinyl acetate) and matrices of a polyanhydride copolymer of a stearic acid dimer and sebacic acid (Sherwood et al., Biotechnology 10, 1446 (1992). The rate of release of a substituted immunolabeling complex from such a matrix depends upon the molecular weight of the substituted immunolabeling complex, the amount of substituted immunolabeling complex within the matrix, and the size of dispersed particles (Saltzman et al., Biophysical J. 55, 163 (1989). Other solid dosage forms are described in REMINGTON'S PHARMACEUTICAL SCIENCES, 18th Ed. (1990). Each of the above-described references is incorporated herein by reference in its entirety.

EXAMPLES

The following examples describe specific aspects of the invention to illustrate the invention and to provide a description of the methods for those of skill in the art. The examples should not be construed as limiting the invention, as the examples merely provide specific methodology useful in understanding and practicing the invention.

Example 1

Preparation of Mouse Fc Antigen

Purified mouse IgG was fragmented with the proteolytic enzyme papain (CURRENT PROTOCOLS IN CELL BIOLOGY, 16.4.1-16.4.10 (2000)). A 12 mL solution of mouse IgG was prepared at ~2 mg/mL in phosphate-buffered saline (PBS). A solution containing 0.1 mg of papain in digestion buffer (PBS, 0.02 M EDTA, 0.02 M cysteine) was added to the antibody and allowed to react at 37° C. for 16 hours. The digestion was terminated by the addition 20 µL of 0.3 M iodoacetamide in PBS. The fragments were dialyzed against 2 L of PBS for 16 hours at 4° C. The Fc fragment was purified on a protein G-Sepharose CL-4B column. The bound fraction containing the Fc fragment was eluted from the column using 50-100 mM glycine/HCl buffer, pH 2.5-2.8. The eluate was collected in 1 mL fractions. The pH of the protein fractions was immediately raised to neutral by addition of 100 µL of either 500 mM phosphate or Tris buffer, pH 7.6, to each 1 mL fraction. The solution was then loaded onto a Sephacryl S-200 Superfine size-exclusion column and fractions corresponding to a molecular weight of ~50 kDa were collected and analyzed by SDS-PAGE and HPLC. The goat anti-(rabbit Fc) fragment was prepared similarly.

Example 2

Goat Anti-(Mouse Fc) Production

To produce polyclonal antibodies, the immunogen used to immunize the animal was the purified mouse or rabbit IgG Fc domain (see Example 1). Methods of immunizing animals are well known and conventional, and suitable immunization protocols and immunogen concentrations can be readily determined by those skilled in the art (Current Protocols in Immunology 2.4.1-9 (1995); ILAR Journal 37, 93 (1995)). Briefly, individual goats were immunized with purified mouse Fc or purified rabbit Fc. The initial immunization in 50% Freund's complete adjuvant (1000 µg conjugate (half subcutaneous, half intramuscularly)) was followed by 500 µg conjugate per goat in Freund's incomplete adjuvant two and four weeks later and at monthly intervals thereafter. Antibodies were harvested from serum using protein A-Sepharose chromatography. Antibodies against mouse Fc isotypes can be prepared by starting with isotype-selected mouse Fc antigens. Rabbits have a single Fc isotype. Characterization of the selectivity and cross-reactivity of isotype-specific antibodies is by standard techniques, including HPLC.

Example 3

Preparation of Fab Fragments

Fragmentation of the goat anti-(mouse Fc) antibody to the monovalent Fab fragment was carried out using the proteolytic enzyme, papain, as described in Example 1. Following dialysis against PBS, the Fab fragment was purified on a protein A-Sepharose CL-4B column. The unbound fraction containing the Fab fragment and the papain was collected. This solution was then loaded onto a Sephacryl S-200 Superfine size-exclusion column and fractions corresponding to a molecular weight of ~50 kDa were collected and analyzed by SDS-PAGE. The Fab fragments of goat anti-(rabbit Fc) can be prepared similarly.

Example 4

Preparation of the Labeled Antibody Immunoglobulin-Binding Protein or the Non-Antibody Immunoglobulin-Binding Peptide and Protein Conjugates in Homogeneous Solution Conjugates of antibody immunoglobulin-binding protein or the non-antibody immunoglobulin-binding peptides or proteins with low molecular weight dyes and haptens such as biotin or digoxigenin are typically prepared from succinimidyl esters of the dye or hapten, although reactive dyes and haptens having other protein-reactive functional groups are also suitable. The typical method for protein conjugation with succinimidyl esters is as follows. Variations in molar ratios of dye-to-protein, protein concentration, time, temperature, buffer composition and other variables that are well known in the art are possible that still yield useful conjugates.

A protein solution of the Fab fragment of goat anti-(rabbit Fc), goat anti-(mouse Fc), protein A, protein G, or protein L or an immunoglobulin-binding peptide (e.g., a peptide identified by screening a library of peptides) is prepared at ~10 mg/mL in 0.1 M sodium bicarbonate (pH ~8.3). The labeling reagents are dissolved in a suitable solvent such as DMF at ~10 mg/mL. Predetermined amounts of the labeling reagents are added to the protein solution with stirring. A molar ratio of 10 moles of dye to 1 mole of protein is typical, though the optimal amount can be varied with the particular labeling reagent, the protein being labeled and the protein's concentration. The optimal ratio was determined empirically. When optimizing the fluorescence yield and determining the effect of degree of substitution (DOS) on the conjugate's brightness, it is typical to vary the ratio of reactive dye to protein over a several-fold range. The reaction mixture is incubated at room temperature for a period that is typically one hour or on ice for several hours. The dye-protein conjugate is typically separated from unreacted reagents by size-exclusion chromatography, such as on BIO-RAD P-30 resin equilibrated with PBS. The initial, protein-containing band is collected and the DOS is determined from the absorbance at the absorbance maximum of each fluorophore, using the extinction coefficient of the free fluorophore. The DOS of nonchromophoric labels, such as biotin, is determined as described in Haugland (Haugland et al., Meth. Mol. Biol. 45, 205 (1995); Haugland, Meth. Mol. Biol. 45, 223 (1995); Haugland, Meth. Mol. Biol. 45, 235 (1995); Haugland, Current Protocols in Cell Biol. 16.5.1-16.5.22 (2000)). Using the above procedures, conjugates of goat anti-(mouse Fc) and goat anti-(rabbit Fc) were prepared with several different Alexa Fluor dyes, with Oregon Green dyes, with biotin-X succinimidyl ester, with desthiobiotin-X succinimidyl ester, with succinimidyl 3-(2-pyridyldithio)propionate (SPDP) and with succinimidyl trans-4-(maleimidylmethyl)cyclohexane-1-carboxylate (SMCC).

Some dye conjugates of protein A and protein G, including those of some Alexa Fluor dyes, are commercially available, such as from Molecular Probes. Inc. (Eugene, Oreg.). The interspecies specificity and approximate affinity of some other non-antibody immunoglobulin-binding proteins bind to segments of a target antibody, such as that of protein A and protein G are known (Langone, Adv. Immunol. 32, 157 (1982); Surolia et al., Trends Biochem. Sci. 7, 74 (1982); Notani et al., J. Histochem. Cytochem. 27, 1438 (1979); Goding, J. Immunol. Meth. 20, 241 (1978); J. Immunol. Meth. 127, 215 (1990); Bjorck et al., J. Immunol. 133, 969 (1984)).

In addition, labeling proteins (goat Fab anti-(mouse Fc), goat Fab anti-(mouse lambda light chain), goat Fab anti-(mouse kappa light chain), protein A, protein G, protein L, lectins, single-chain fragment variable antibodies (ScFv) ) conjugated to the detectable labels of R-phycoerythrin (R-PE), allophycocyanin (APC), tandem conjugates of phycobiliproteins with chemical dyes including several Alexa Fluor dyes, horseradish peroxidase (HRP), *Coprinus cinereus* peroxidase, *Arthromyces ramosus* peroxidase, glucose oxidase and alkaline phosphatase (AP) were or can be prepared by standard means (Haugland et al., Meth. Mol. Biol. 45, 205 (1995); Haugland, Meth. Mol. Biol. 45, 223 (1995); Haugland, Meth. Mol. Biol. 45, 235 (1995); Haugland, Current Protocols in Cell Biol 16.5.1-16.5.22 (2000)). Fusion proteins, such as of protein G or protein A with detectable labels such as luciferin, aequorin, green-fluorescent protein and alkaline phosphatase are also known that are suitable for practice of the invention (Sun et al., J. Immunol. Meth. 152, 43 (1992); Eliasson et al., J. Biol. Chem. 263, 4323 (1988); Eliasson et al., J. Immunol. 142, 575 (1989)).

Immunoglobulin heavy and light chains, like most secreted and membrane bound proteins, are synthesized on membrane-bound ribosomes in the rough endoplasmic endoplasmic reticulum where N-linked glycosylation occurs. The specificity of lectins for carbohydrates, including N-linked glycoproteins, is also known (EY laboratories, Inc. Lectin Conjugates Catalog, 1998).

Example 5

Preparation of the Labeled Antibody Immunoglobulin-Binding Protein or the Non-Antibody Immunoglobulin-Binding Peptide and Protein Conjugates while Bound to an Affinity Matrix Unlabeled Fab fragment for goat anti-(mouse Fc) (prepared as in Example 3) was bound to agarose-immobilized mouse IgG for one hour. Following a wash step with bicarbonate buffer, pH 8.3, the complex of immobilized IgG and unlabeled Fab was labeled for one hour at room temperature with the succinimidyl ester of the amine-reactive label. Unconjugated dye was eluted with bicarbonate buffer, and then the covalently labeled Fab fragment was eluted with 50-100 mM glycine/HCl buffer, pH 2.5-2.8. The eluate was collected in 1 mL fractions. The pH of the protein fractions was immediately raised to neutral by addition of 100 µL of either 500 mM phosphate or Tris buffer, pH 7.6, to each 1 mL fraction. Variations of the reagent concentrations, labeling times, buffer composition, elution methods and other variables are possible that can yield equivalent results. Conjugates of the Fab fragment of goat anti-(rabbit Fc) and of protein G and protein A are prepared similarly.

Example 6

Comparison of the Alexa Fluor 488 Dye-Labeled Fab Fragments of Goat Anti-(Mouse Fc) Prepared as in Example 4 and as in Example 5

Conjugates of the Fab fragment of goat anti-(mouse Fc) with the Alexa Fluor 488 succinimidyl ester were separately prepared, as described in Examples 4 and 5. The conjugates had estimated degrees of substitution of ~1.9 (labeled as in Example 4) and ~3.0 (labeled as in Example 5), respectively, and virtually identical absorption and emission spectral maxima. When excited at 488 nm, conjugates prepared using the fragment prepared as described in Example 5 were about 3.2-times more fluorescent than using the fragments that were prepared in Example 4 (FIG. 8) as detected by flow cytometry when bound to CD3 on Jurkat T cells. Similar results were observed with other dyes.

Example 7

Preparation of a Labeling Protein from Protein G and Albumins

Native protein G has a high affinity binding (nanomolar) site for albumins, in particular ovalbumin. Equal weights of protein G and Texas Red ovalbumin (Molecular Probes. Inc.) were dissolved in PBS, pH 7.5. After one hour, the resulting complex was separated on a Sephacryl S-200 Superfine size-exclusion column and analyzed by SDS-PAGE and HPLC. Alternatively, the protein G is combined with a labeled albumin while the protein G is immobilized on any of the several immunoglobulins to which it binds, and the excess labeled albumin is washed away preceding elution of the albumin-labeled protein G complex from the matrix.

Example 8

Preparation of an Immunolabeling Complex on a Very Small Scale

Submicrogram quantities of a target-binding antibody were complexed with submicrograms of a labeling protein in varying molar ratios of between about 1:1 and 1:20 to prepare an immunolabeling complex that was suitable for staining a sample. For instance, 0.1 µg of mouse monoclonal anti-α-tubulin in 1 µL PBS with 0.1% BSA was complexed with 0.5 µg of the Alexa Fluor 488 dye-labeled Fab fragment of goat anti-(mouse Fc) (prepared as in Example 4) or with 0.1 µg of the Alexa Fluor 488 dye-labeled Fab fragment of goat anti-(mouse Fc) (prepared as in Example 5) in 5 µL of PBS for 10 minutes at room temperature. The immunolabeling complex can be used immediately for staining tubulin in fixed-cell preparations (Example 16) or any excess unbound Alexa Fluor 488 dye-labeled Fab fragment of goat anti-(mouse Fc) in the immunolabeling complex can be captured with nonimmune mouse IgG (Example 9) for combination with other antibody conjugates, including those of targeting antibodies that have been directly conjugated to other labels. Rabbit antibodies were labeled similarly using labeled goat anti-(rabbit Fc). Labeling of targeting antibodies with a labeled protein A, protein L, protein G, protein G complexed with a labeled albumin, or other immunoglobulin-binding peptides or proteins proceeds similarly. In the case of a mouse (or rat) monoclonal antibody, it is preferred to use a labeled protein that is selective for the specific isotype of the primary antibody (e.g. anti-(mouse $IgG_1$) for a mouse $IgG_1$ isotype primary antibody). Although some cross-reactivity for other mouse (or rat) isotypes was observed using a goat antibody that was selective for mouse $IgG_1$ isotype monoclonal antibodies, routine and optimal use for labeling unmatched mouse isotypes required greater amounts of immunolabeling complexes and was somewhat less reliable.

Example 9

Capturing Excess Immunoglobulin-Binding Protein by a Capturing Component

Figure 2:
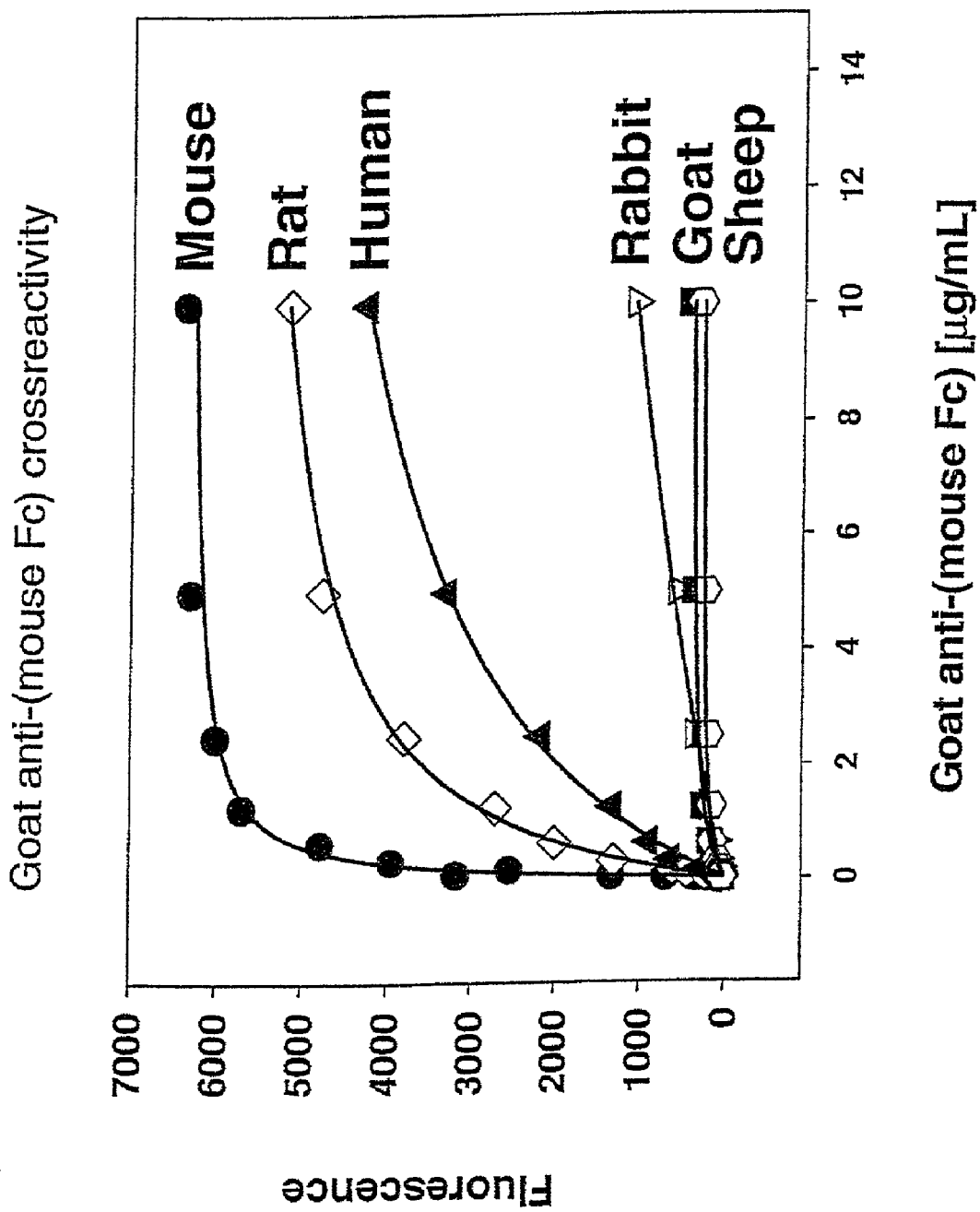
FIG. 2 graphically represents species specificity of goat Fab anti-(mouse Fc), as observed using a microplate coated with IgG of various species. The various species were blocked with BSA, reacted with biotinylated goat Fab anti-(mouse Fc), washed, and then treated with streptavidin-horseradish peroxidase (HRP), followed by hydrogen peroxide ($H_2O_2$) and the Amplex Red peroxidase detection reagent.

Immunolabeling complexes were prepared as described in Example 8. To the immunolabeling complex was added to each tube 25 µL of a 14.1 mg/mL stock solution of unlabeled mouse IgG to capture excess immunolabeling complexes. As shown in FIG. 1, not all of the immunoglobulin-binding protein was necessarily complexed with the target-binding antibody to form an immunolabeling complex. Consequently, particularly for applications in which labeling complexes of multiple primary antibodies from the same species (e.g. mouse monoclonal antibodies) or crossreacting species (e.g. mouse and human antibodies, FIG. 2, Table 1) were to be used simultaneously or sequentially, it is necessary to quench or otherwise remove any excess immunoglobulin-binding protein by use of a capturing component or by other means to avoid inappropriate labeling of the sample. The most effective capturing component to capture excess immunoglobulin-binding protein is one that contains the binding site of the targeting agent. For instance, whole mouse IgG or mouse serum was shown to be an effective and inexpensive reagent when the immunoglobulin-binding protein was bound to a segment of a mouse monoclonal antibody. The mouse IgG was added in excess to the amount of immunoglobulin-binding protein and incubated for a period of approximately 1-5 minutes, or longer.

It is preferred to prepare the immunolabeling complex and then add the capturing component shortly before the experiment. The rapid quenching effect permits this to be done within minutes of performing labeling of the sample by the immunolabeling complex. If desired, the excess capturing component can be removed following labeling of the sample by a simple wash step. Alternatively, fixation of the stained sample by aldehyde-based fixatives or other reagents or methods subsequent to incubation with the immunolabeling complex can provide permanent immobilization of the immunolabeling complex on its target in the sample. As an alternative to adding a soluble capturing component to the immunolabeling complex, the capturing component can be immobilized on an insoluble matrix such as agarose and the immunolabeling complex contacted with that matrix. A preferred matrix when labeling mouse antibodies to mouse antigens is mouse IgG immobilized on agarose. Excess labeled anti-rabbit antibodies can be captured using rabbit IgG that is free in solution or immobilized. Alternatively, the immunolabeling complex can be separated from any capturing component by chromatographic or electrophoretic means.

Example 10

HPLC Analysis of a Labeling Complex

Figure 6:
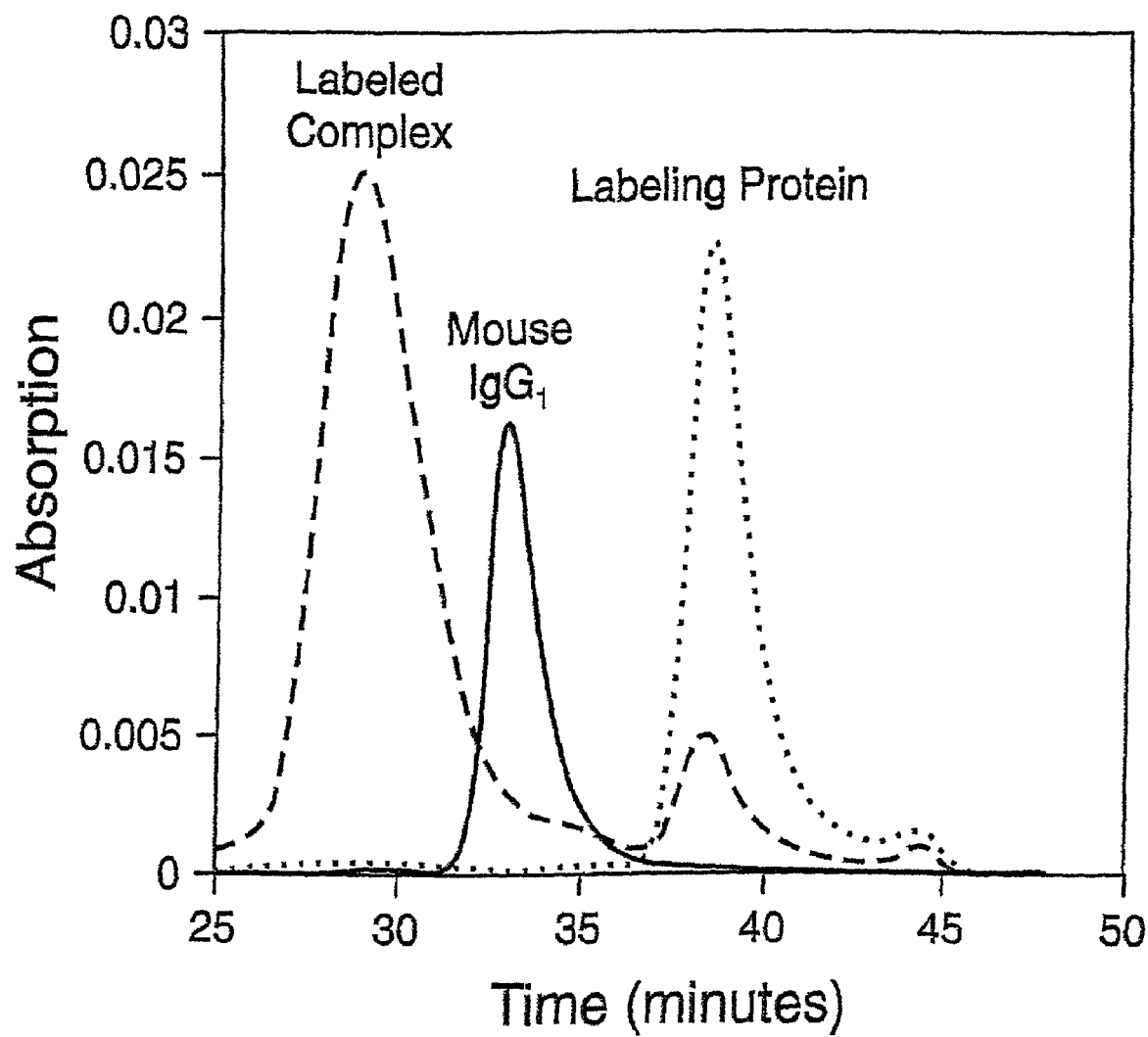
FIG. 6 illustrates high-performance size-exclusion chromatographic analysis of Alexa Fluor 488 dye-labeled goat Fab anti-(mouse Fc) labeling protein binding to a mouse $IgG_1$ target-binding antibody. The labeling protein, alone, appears as a peak at 38 minutes; the target-binding antibody, alone, appears as a peak at 33 minutes. When labeling protein and target-binding antibody are mixed together at a molar ratio of ~5:1 (labeling protein:target-binding antibody), the resulting immunolabeling complex appears as a peak at 29 minutes (Example 10).
Figure 7:
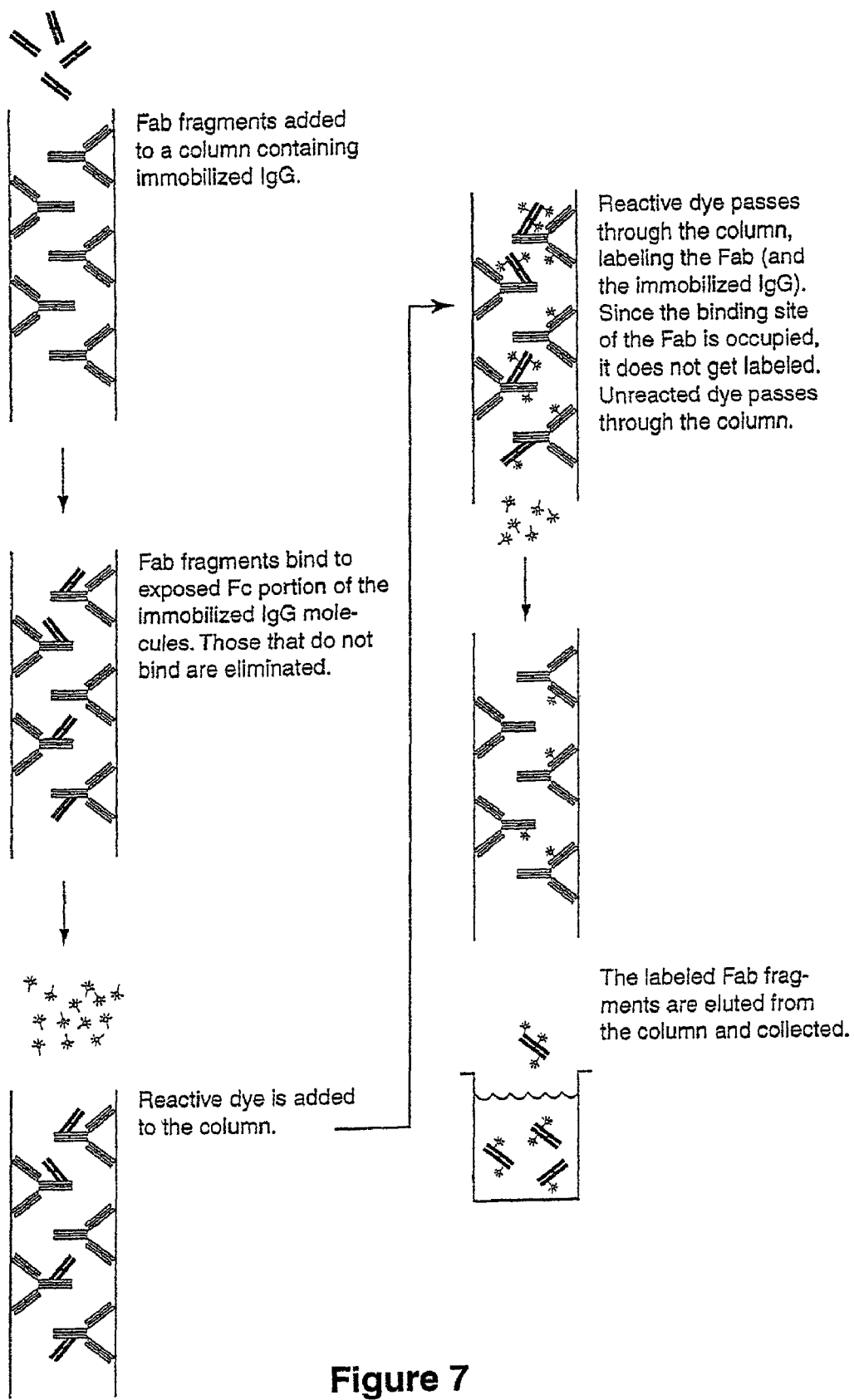
FIG. 7 is a cartoon depiction of the process for preparing improved labeling proteins.

In order to analyze the success and extent of complex formation of the labeling protein with the target-binding antibody, size exclusion HPLC of the samples was performed. For instance, a complex of Alexa Fluor 488 dye-labeled goat Fab anti-(mouse Fc) with a monoclonal mouse anti-tubulin in molar ratios of approximately 1:1, 3:1, 5:1 and 10:1. These were separated by analytical HPLC using a BioSep S-3000 column and eluting with 0.1 M $NaP_i$, 0.1 M NaCl, pH 6.8, at a flow rate of 0.25 mLs/min. An example of the separation using the 5:1 molar ratio (FIG. 6) demonstrates that, using this molar ratio, formation of the labeled complex is essentially quantitative.

Example 11

Cross-Reactivity of Goat Fab Anti-(Mouse Fc) to Other Species of IgG

Microplates were equilibrated overnight with IgG from a mouse or non-mouse species, and then further blocked with BSA. Variable amounts of the biotinylated Fab fragment of goat anti-(mouse Fc) were added to each well and allowed to bind. After washing, streptavidin-HRP and the Amplex Red peroxidase substrate were added. HRP activity was detected by the addition of $H_2O_2$ using the Amplex Red Peroxidase Assay Kit (Molecular Probes, Inc., Eugene, Oreg.). Reactions containing 200 µM Amplex Red reagent, 1 U/mL HRP and 1 mM $H_2O_2$ (3% solution) in 50 mM sodium phosphate buffer, pH 7.4, were incubated for 30 minutes at room temperature. Fluorescence was measured with a fluorescence microplate reader using excitation at 560±10 nm and fluorescence detection at 590±10 nm. Background fluorescence, determined for a no-$H_2O_2$ control reaction, was subtracted from each value (Table 1 and FIG. 2). Table 1 shows that the goat anti-(mouse Fc) antibody because of the highly conserved structure of the Fc region of an antibody it can be used to complex other non-mouse antibodies, including rat, and human antibodies. The goat anti-mouse IgG antibody reaction with mouse antibody was set at 100% and the crossreacting antibodies were expressed as a percentage compared the mouse on mouse data. The data in Table 1 show that the Fab fragment of the goat anti-(mouse Fc) antibody of the current invention does not strongly bind to the goat or sheep Fc domain; however, one skilled in the art could generate antibodies that will react with the goat and sheep Fc domain or the Fc domain of any other species. Biotinylated Fab goat anti-(mouse Fc) was used in this example because it provided a convenient method to quantitate the amount of crossreactivity in a conventional method but it could have been accomplished using a fluorophore Fab labeled goat anti-(mouse Fc). It was demonstrated by HPLC (as in Example 10) that Alexa Fluor 488 dye-labeled goat anti-(rabbit Fc) bound to rabbit primary antibodies.

TABLE 1

Cross-reactivity of goat anti-mouse IgG antibody with other non-mouse antibodies.

| Species | Crossreactivity | % Fluorescence |
|---|---|---|
| Mouse | ++++ | 100 |
| Rat | +++ | 80.7 |
| Human | ++ | 66.7 |
| Rabbit | + | 16.9 |
| Goat | − | 6.5 |
| Sheep | − | 5.7 |

Example 12

Figure 3:
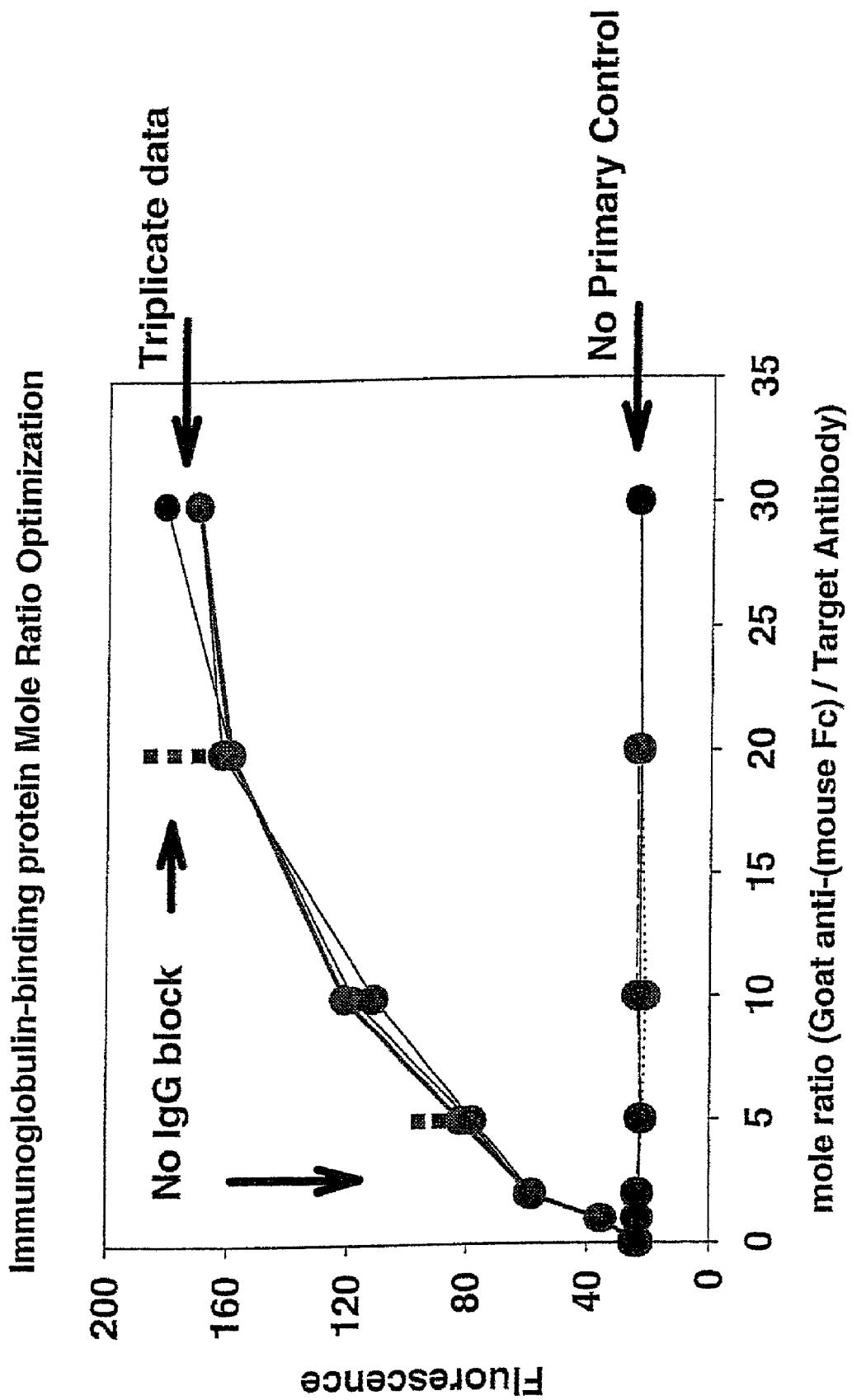
FIG. 3 graphically depicts the optimal molar ratio of a goat Fab anti-(mouse Fc) protein. Varying amounts of an Alexa Fluor 488 dye-labeled Fab fragment of goat anti-(mouse Fc) were added to a constant amount of anti-biotin monoclonal antibody (mAb). This mixture was equilibrated for 20 minutes, and then added to biotinylated-BSA in a microplate well. After allowing time to bind, the plates were washed and the remaining fluorescence was quantitated. The analysis was performed in triplicate (circles). Control experiments were performed, as described above, but without adding the primary anti-biotin antibody (solid squares).
Figure 4:
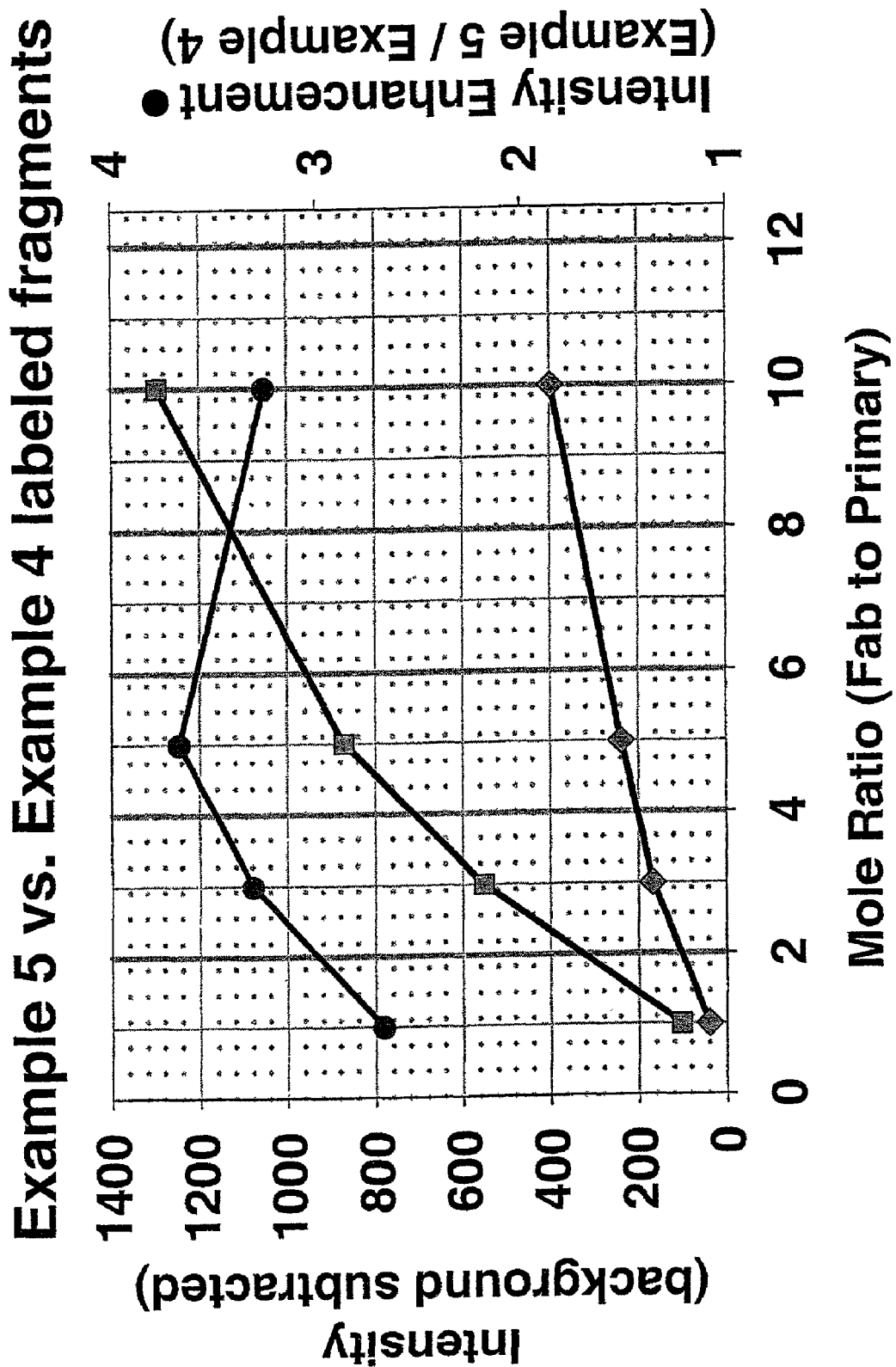
FIG. 4 illustrates a comparison of the fluorescence intensity (Example 6) for labeling protein prepared in homogeneous solution (Example 4) and labeling protein prepared on a column (Example 5).

Determination of the Optimal Molar Ratio of Immunoglobulin-Binding Protein to Target Antibody Using a Microplate Assay To 1.6 µg of mouse monoclonal anti-biotin (MW 145,000) in 8.0 µL PBS was added varying amounts of the Alexa Fluor 488 dye-labeled Fab fragment of goat anti-(mouse Fc) (MW ~50,000) (prepared as in Example 4) to form an immunolabeling complex. After equilibration for 20 min, a 100 µL aliquot was added to a 96-well microplate coated with biotinylated BSA. After 30 minutes, the plates were washed and the residual fluorescence was quantitated using a fluorescence microplate reader using excitation at 485+/−10 nm and detecting emission at 530+/−12.5 nm. As shown in FIG. 3, a molar ratio of the Alexa Fluor 488 dye-labeled Fab fragment of goat anti-(mouse Fc) to the anti-biotin between 5 to 20 was sufficient to form appreciably detectable complexes (FIG. 3; fluorescence quantitated, performed in triplicate (circles); control experiments performed but without adding the primary anti-biotin antibody (solid squares)). A molar ratio of about 5 to about 10 was preferred for this pair of immunoglobulin-binding protein and target antibody. This ratio can be varied somewhat to increase or decrease the signal or to affect the consumption of valuable reagents. The weight ratio of immunoglobulin-binding protein to target-binding antibody is particularly affected by the actual molecular weight of the immunoglobulin-binding protein.

For instance, equal weights of the dye-labeled goat Fab anti-(mouse Fc) (prepared as in Example 5) and an intact mouse primary antibody, which corresponds to an approximately 3 to 1 molar ratio, usually yields suitable labeling complexes. Fluorescence intensity (or enzymatic activity) of the immunolabeling complex is readily adjusted by a corresponding adjustment of the amount of labeled Fab fragment used.

Similar analyses of the ratio for other labeling proteins (including those of labeled protein A, protein G, protein L, IgG-binding peptides and antibodies to other segments of the primary antibody), and for conjugates of labels other than Alexa Fluor 488 dye (including enzymes in combination with the appropriate enzyme substrates) are done essentially as described in this example.

Example 13

Dissociation Rate of the Immunolabeling Complex

A pre-equilibrated immunolabeling complex was prepared from 50 µg of an Alexa Fluor 488 dye-labeled Fab fragment of goat anti-(mouse Fc) and 15 µg of an anti-biotin monoclonal antibody (mAb). The immunolabeling complex was rapidly diluted with capturing component sufficient to give a 6.2 molar excess over the anti-biotin mAb. At various times, an aliquot was taken and added to a microplate well containing an excess of biotinylated BSA. After 30 minutes, the plates were washed and the remaining fluorescence was quantitated. Displacement of the labeling protein from the target-binding antibody through exchange was measured by any time-dependent decrease in fluorescence in the microplate well. For example the fragments prepared as described in Example 4 had 68 percent fragments bound to the target-binding antibody after 30 minutes compared to 87 percent of bound fragments that were prepared according to Example 5. One hour showed a similar decrease, 56 percent and 68 percent respectively. The labeling protein was shown to undergo a stable interaction with the target-binding antibody, with a lifetime for half exchange under these conditions of 3.5 hours. Dissociation rates were measured for labeling protein prepared according to Example 4 and for labeling protein prepared according to Example 5, demonstrating the greater stability of immunolabeling complexes made using the labeling proteins prepared according to Example 5.

Example 14

Protocol for Staining Cultured Cells with a Single Immunolabeling Complex

Culturable cells, such as bovine pulmonary artery endothelial cells (BPAEC), were grown on a 22×22 mm glass coverslip. The cells were fixed for 10 minutes using 3.7% formaldehyde in DMEM with fetal calf serum (FCS) at 37° C. The fixed cells were washed 3 times with PBS. The cells were permeabilized for 10 min with 0.02% Triton X-100 in PBS, washed 3× with PBS and blocked for 30 min with 1% BSA in PBS. Variations of the cell type and cell preparation, fixation, and permeabilization methods, including methods for antigen retrieval, are well known to scientists familiar with the art. An immunolabeling complex was prepared as described in Example 8. The immunolabeling complex was added directly to the fixed and permeabilized cells in an amount sufficient to give a detectable signal if there is a binding site for the primary antibody present in the sample. After an incubation period that was typically 10-60 minutes (usually about 15-30 minutes), the cells were washed with fresh medium and the labeling was evaluated by methods suitable for detection of the label. Staining by the immunolabeling complex can be additionally preceded, followed by or combined with staining by additional reagents, such as DAPI, which yields blue-fluorescent nuclei.

Example 15

Protocol for Staining Cultured Cells with Multiple Immunolabeling Complexes

Cells were fixed and permeabilized as described in Example 14. Multiple immunolabeling complexes were individually prepared from a variety of labeling proteins, according to the procedure described in Example 8. The multiple immunolabeling complexes were either used individually or sequentially to stain the cells, according to the procedure described in Example 14, or two or more immunolabeling complexes were formed then co-mixed in a single staining solution and used to simultaneously stain the sample. The optimal method for cell fixation and permeabilization and the best ratio for combination of the immunolabeling complexes are typically determined by preliminary experimentation using single immunolabeling complexes or multiple immunolabeling complexes used in combination. A first immunolabeling complex was prepared from an Alexa Fluor 488 dye-labeled Fab fragment of goat anti-(mouse Fc) and mouse monoclonal anti-α-tubulin, a second immunolabeling complex was prepared from an Alexa Fluor 568 dye-labeled Fab fragment of goat anti-(mouse Fc) and mouse monoclonal anti-vimentin (anti-vimentin was an ascites fluid preparation) and a third immunolabeling complex was prepared from an Alexa Fluor 647 dye-labeled Fab fragment of goat anti-(mouse Fc) and mouse monoclonal anti-cdc6 peptide antibody (Molecular Probes). Aliquots of the three different immunolabeling complexes were combined and used to stain BPAE cells for 30 minutes, washed with fresh medium and observed by fluorescence microscopy using optical filters appropriate for the three dyes. In this example, some cells showed cytoplasmic staining by the anti-vimentin antibody, nuclear staining by the anti-cdc6 peptide antibody and staining of mitotic spindles by the anti-α-tubulin antibody, indicative of a cell in mitosis. Staining by the immunolabeling complexes was additionally preceded, followed by or combined with staining by additional reagents, such as Alexa Fluor 350 phalloidin, which yielded blue-fluorescent actin filaments in the above example.

The immunolabeling complexes that are used in combination do not have to be targeted toward antibodies from the same species. For instance, complexes of Alexa Fluor 488 dye-labeled goat anti-(mouse $IgG_1$ Fc) with a mouse $IgG_1$ monoclonal target-binding antibody and an Alexa Fluor 594 dye-labeled goat anti-(rabbit Fc) with a rabbit primary target-binding antibody can be prepared and used in combined staining protocols.

Example 16

Protocol for Staining Tissue with a Single Immunolabeling Complex

A mouse intestine cryosection (University of Oregon histology core facility), a cross-section of about 16 µm thickness, was mounted on a slide. The intestine was perfused and fixed with 4% formaldehyde prior to dissection, embedding, and sectioning. The tissue section was rehydrated for 20 minutes in PBS. An immunolabeling complex was prepared as described in Example 8. Briefly, 0.1 µg of mouse monoclonal anti-cdc6 peptide (a nuclear antigen) in 1 µL PBS with 0.1% BSA was complexed with 0.5 µg of the Alexa Fluor 350 dye-labeled Fab fragment of goat anti-(mouse $IgG_1$ Fc) (prepared as in Example 4) in 5 µL of PBS for 10 minutes at room temperature. Excess Fab fragment of goat anti-(mouse $IgG_1$ Fc) was captured with 25 µL of a 14.1 mg/mL stock of unlabeled mouse IgG. The tissue was permeabilized with 0.1% Triton X-100 for 10 min.

The tissue was washed two times with PBS and was blocked in 1% BSA for 30 min. The immunolabeling complex was added directly to the tissue for 30 minutes and washed three times in PBS. The sample was mounted in Molecular Probes' Prolong antifade mounting medium and observed by fluorescence microscopy using optical filters appropriate for the Alexa Fluor 350 dye. Results showed that the mouse monoclonal anti-cdc6 peptide immunolabeling complex showed specific nuclear labeling in the mouse intestine tissue section. Variations of the tissue type and tissue preparation, fixation and permeabilization methods, mounting methods, including methods for antigen retrieval, are well known to scientists familiar with the art.

Example 17

Staining of a Tissue Target in Combination with Tyramide Signal Amplification (TSA)

Mouse brain cryosections were labeled with a pre-formed complex of horseradish peroxidase (HRP)-labeled goat anti-(mouse $IgG_1$ Fc) antibody and a mouse $IgG_1$ monoclonal anti-(glial fibrillary acidic protein (GFAP)) prepared essentially as in Example 8 using a molar ratio of labeling protein to monoclonal antibody of 3. Staining of the mouse tissues was essentially as in Example 16. The staining localization and intensity was compared to that of (a) goat anti-mouse IgG HRP conjugate and mouse anti-GFAP, (b) the Alexa Fluor 488 dye-labeled Fab fragment of goat anti-mouse $IgG_1$ Fc) antibody complex of mouse anti-GFAP, (c) Alexa Fluor 488 goat anti-mouse IgG secondary antibody and mouse anti-GFAP, and (d) a direct conjugate of the Alexa Fluor 488 dye with mouse anti-GFAP. The HRP-conjugated probes were incubated with Alexa Fluor 488 tyramide using TSA Kit #2 (Molecular Probes, Inc.) according to standard procedures. The tissue staining patterns in each case were similar and consistent with the expected staining pattern of mouse anti-GFAP and staining was essentially free of nonspecific background. The relative fluorescence intensities of staining measured by digital imaging were sequentially: 541 relative intensity units for the HRP-goat anti-(mouse $IgG_1$ Fc) complex of mouse anti-GFAP and (using the combinations indicated by the letters above): (a) 539, (b) 234, (c) 294, and (d) 255 relative intensity units.

Example 18

Staining of Live Cells by Multiple Immunolabeling Complexes

Figure 5A:
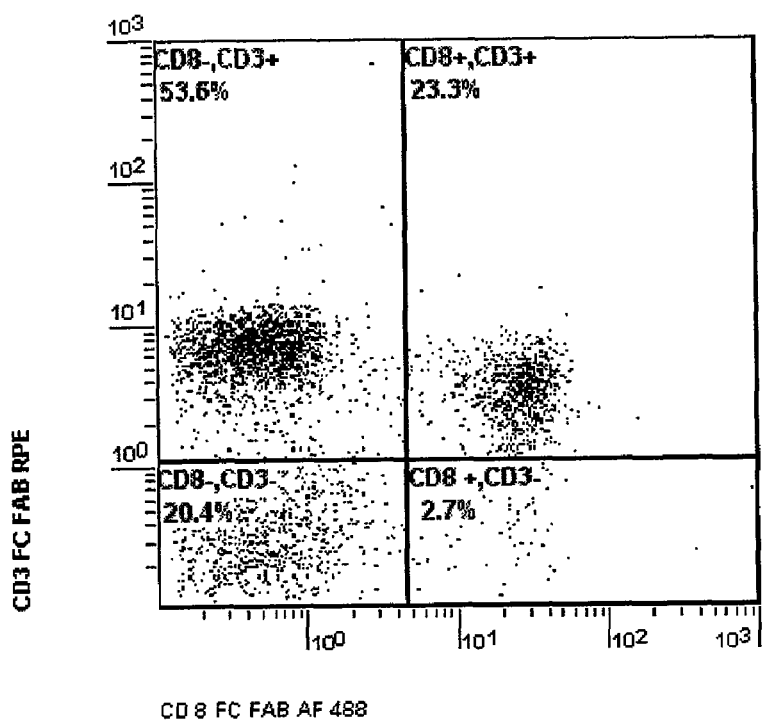
FIG. 5A: CD3-positive R-phycoerythrin (R-PE) stained T cells are shown in the upper left (UL) and upper right (UR) quadrants (Example 18). The relative percentages of total lymphocytes that are CD3-positive cells are 83.3% (UL+UR). The relative percentage of CD8-positive Alexa Fluor 488 dye-stained lymphocytes and CD3-positive R-PE dye-stained lymphocytes is 35.1% (UR quadrant). The lower left quadrant (LL, 20.4%) shows CD3-negative lymphocytes (i.e. non-T cells) comprised of NK cells, B cells and some monocytes. In the lower right (LR, 2.7%) region are non-T cells, which are nonspecifically stained.
Figure 5B:
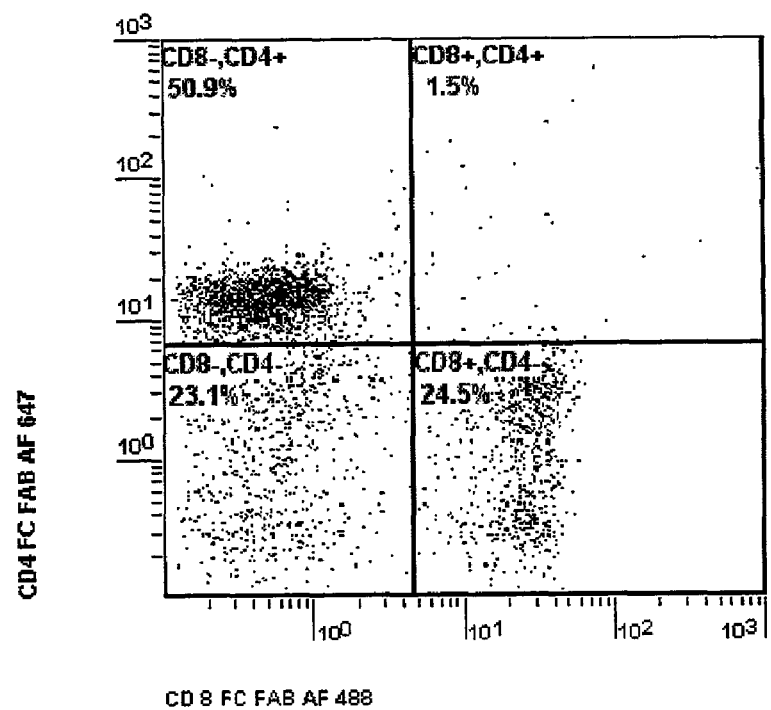
FIG. 5B: CD3-positive T-cells are subdivided into Alexa Fluor 647 CD4-positive and Alexa Fluor 488 CD8-positive (Example 18). CD4-positive cells represent 50.9% of total lymphocytes (UL quadrant) and CD8-positive cells represent 24.5% of the total lymphocytes (LR quadrant). The 23.1% of cells in the LL quadrant are non-T cells, while the 1.5% of cells in UR quadrant are likely nonspecifically stained lymphocytes.

A first immunolabeling complex was prepared from an Alexa Fluor 488 dye-labeled Fab fragment of goat anti-(mouse $IgG_1$ Fc) and mouse monoclonal anti-(human CD8), a second immunolabeling complex was prepared from an R-phycoerythrin-conjugated Fab fragment of goat anti-(mouse $IgG_1$ Fc) and mouse anti-(human CD3), and a third immunolabeling complex was prepared from an Alexa Fluor 647 dye-labeled Fab fragment of goat anti-(mouse $IgG_1$ Fc) and mouse anti-(human CD4). The complexes were prepared as described in Example 8 and were each blocked with 20 µg (1.3 µL of 14.1 µg/mL) of mouse IgG for 10 minutes at room temperature. The first immunolabeling complex was added to 100 µL of whole blood and incubated for 15 min. The cells were washed with PBS and 280.5 µL of the second immunolabeling complex was added and incubated for 15 min. The cells were again washed, and 46.2 µL of the third labeling complex was added and incubated for 15 min. After the final incubation, the red blood cells were lysed with cell-lysis buffer. The cells were resuspended in 1% formaldehyde/PBS and analyzed on a FACS Vantage flow cytometer using a 488 nm argon-ion laser for excitation of the first and second immunolabeling complexes and a 633 nm red He—Ne laser for excitation of the third immunolabeling complex (FIGS. 5a, 5b). The emission band pass filters used for selective detection of the dyes are 525+/−10 nm for the Alexa Fluor 488 (CD8), 585+/−21 nm for R-PE (CD3) and 675+/−10 nm for the Alexa Fluor 647 dye (CD4). FIGS. 5a and 5b show that the instant invention can be used in a 3-color immunophenotyping experiment using peripheral blood lymphocytes. CD3-positive T cells were stained with the R-phycoerythrin-conjugated Fab fragment of goat anti-(mouse Fc) and mouse anti-human CD3), upper left (UL) quadrant, FIG. 5a. CD4-positive cells, a T cell subset, are identified using Alexa Fluor 647 dye-labeled Fab fragment of goat anti-(mouse IgG$_1$ Fc)

dividing the FL1 and FL4 channel intensities for such combinations by the intensities of the 100% Alexa Fluor 488 dye- and 100% Alexa Fluor 647 dye-labeled cells, respectively.

TABLE 2

Theoretical versus recovered dye-labeled Fab fragment of goat anti-(mouse IgG$_1$ Fc) combinatorial experiment.

| Experimentally mixed percentage of cells labeled with Alexa Fluor 488 dye-labeled Fab fragment of goat anti-(mouse IgG$_1$ Fc) | Recovered percentage of measured cells labeled with Alexa Fluor 488 dye-labeled Fab fragment of goat anti-(mouse IgG$_1$ Fc) | Experimentally mixed percentage of cells labeled with Alexa Fluor 647 dye-labeled Fab fragment of goat anti-(mouse IgG$_1$ Fc) | Recovered percentage of measured cells labeled with Alexa Fluor 647 dye-labeled Fab fragment of goat anti-(mouse IgG$_1$ Fc) |
| --- | --- | --- | --- |
| 100% | 100% | 0% | 0% |
| 75% | 81% | 25% | 14% |
| 50% | 63% | 50% | 38% |
| 25% | 35% | 75% | 73% |
| 0% | 0% | 100% | 100% | and mouse anti-(human CD4), UL quadrant, FIG. 5b and CD8-positive T cells, a T cell subset, were identified using Alexa Fluor 488 dye-labeled Fab fragment of goat anti-(mouse IgG$_1$ Fc) and mouse monoclonal anti-(human CD8), lower right (LR) quadrant, FIG. 5b.

Exposed antigens of live cells, including cultured cells and cells from biological fluids such as blood and cerebrospinal fluid can be simultaneously or sequentially stained by combinations of immunolabeling complexes, including antibodies to the same target labeled with two or more separately detectable immunoglobulin-binding proteins.

Example 19

The Dye-Labeled Fab Fragment of Goat Anti-(Mouse Fc) can be Utilized for the Combinatorial Labeling of Primary Antibodies, to Generate a Multitude of Colored Targets A first immunolabeling complex was made by combining 2.5 μg Alexa Fluor 488 dye-labeled Fab fragment of goat anti-(mouse IgG$_1$ Fc) with 0.5 μg mouse anti-human CD3 (Caltag at 200 μg/mL), according to the procedure described in Example 4. A second immunolabeling complex was made by combining 5.0 μg Alexa Fluor 647 dye-labeled Fab fragment of goat anti-(mouse IgG$_1$ Fc) with 0.5 μg mouse anti-human CD3, according to the procedure in Example 4. Each complex was separately incubated at room temperature for 5 minutes, and each complex was then separately combined with an excess of mouse IgG (14.1 mg/mL) for 5 min at room temperature to capture excess unbound dye-labeled Fab fragments. The two immunolabeling complexes were then added in different percentage combinations (see Table 2) to 100 μL of washed heparinized blood. The cells were incubated with the respective combinations of complexes for 20 min on ice. The red blood cells were then lysed with a cell-lysis buffer. The cells were resuspended in 1% formaldehyde/PBS and analyzed on a FacVantage flow cytometer using a 488 nm argon 633 HeNe laser for excitation and a 530+/−10 nm band pass emission filter (FL1), and a 640 long pass filter (FL4). Five samples of different combined percentages (Table 2) were compared by flow cytometry, with signals being collected in FL1 and FL4. To determine the percentage of cells detected with each type of emission, the FL1 and FL4 intensities for each percentage combination were normalized by Example 20

The Immunolabeling Complex can be used to Detect Antigens on a Western Blot

Bovine heart mitochondria were isolated (Hanson et al., Electrophoresis 22, 950 (2001)). The isolated mitochondria were resuspended to ~10 mg/mL in 100 mM Tris-HCl, pH 7.8, 1 mM phenylmethylsulfonyl fluoride (a protease inhibitor), 2% SDS and insoluble material was removed by centrifugation for 10 minutes at 10,000×g in a tabletop centrifuge. The protein concentration of the lysate was checked by the BCA assay (Pierce, Rockford, Ill.). Samples for gel electrophoresis were prepared by mixing lysate, water, and loading buffer to the appropriate concentrations (final concentration of loading buffer in samples: 58 mM Tris/HCl, 10% glycerol, 2% SDS, 0.02 mg/mL bromphenol blue, 50 mM DTT, pH 8.6). The samples were then heated to 90° C. for 5 minutes before loading on the gel and separated on a 13% SDS-PAGE gel. Two-fold serial dilution of the extracts ranging from 8 μg of extract down to 0.03 μg were loaded on the SDS-PAGE gel. The proteins were transferred to PVDF membrane for 1.5 hours using a semi-dry transfer system according to manufacturer's directions (The W.E.P. Company, Concord, Calif.). The PVDF membrane was blocked for 1 hour in 5% milk.

Immunolabeling complexes were made with mouse monoclonal antibodies that recognize two different mitochondrial proteins. Alexa Fluor 647 dye-labeled Fab fragment of goat anti-(mouse IgG$_1$ Fc) (5 μL of a 1 mg/mL stock, prepared as in Example 4) was incubated with 21 μL (0.88 mg/mL) mouse anti-(CV-alpha) and Alexa Fluor 488 dye-labeled Fab fragment of goat anti-(mouse IgG$_1$ Fc) (5 μL of a 1 mg/mL stock, prepared as in Example 4) was incubated with 19 μL (0.88 mg/mL) mouse anti-(CIII-core2) (Molecular Probes, Eugene, Oreg.). Following a 30 minute incubation, 25 μL of a 14.1 mg/mL stock of unlabeled mouse IgG was added to each tube. The immunolabeling complexes were then mixed together and brought up to 5 mL in 5% milk. The blot was incubated with the mixture of immunolabeling complexes for 1 hour at room temperature. The blot was washed twice for 5 seconds each with PBST (PBS with 0.1% Tween) and once with PBST for 15 minutes. The blot was air dried and imaged on an EG&G Wallac Imager with the appropriate filters. The Western blot revealed two distinct bands of the appropriate molecular weight. The Western blot also showed that no cross-labeling of the antibodies occurred and the detection limit was 125 ng.

Example 21

High-Throughput Screening of Hybridomas for Identifying High Affinity and High IgG Producers Microplate wells containing both a fluorescent labeled antigen of one fluorescent color label and fluorescently labeled Fab fragments of goat anti-(mouse Fc) of a different fluorescent color made by the method described in Example 4 and 5. Hybridoma supernatant is harvested and added to the wells. If the hybridoma are producing the desired antibody, i.e. antibodies that bind to the labeled antigen, polarization of the florescence corresponding to the labeled antigen will allow visualization of those wells containing antigen specific antibody. In addition, the amount of IgG which the hybridomas produce, can be simultaneously identified by polarization of the fluorescence corresponding to the labeled Fab fragments. This method thus allows for both quantitation of the amount of antibody present in a specific amount of hybridoma supernatant and the affinity of the monoclonal antibodies for the antigen.

The reagents employed in the preceding examples are commercially available or can be prepared using commercially available instrumentation, methods, or reagents known in the art or whose preparation is described in the examples. It is evident from the above description and results that the subject invention is greatly superior to the presently available methods for determining the presence of a target in a biological sample. The subject invention overcomes the shortcomings of the currently used methods by allowing small quantities of antibodies to be labeled and in unlimited media while maintaining specificity and sensitivity. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications and patent applications mentioned in this specification are herein incorporated by reference to the same extent as if each individual publication or patent application was specifically and individually indicated to be incorporated by reference.

What is claimed is:

1. A method for determining the presence of a desired target in a biological sample, said method comprising:
    a) combining in a reaction vessel, at least one target-binding antibody comprising an Fc region with a labeling protein to form a labeling mixture, wherein the target-binding antibody is capable of binding to the target, and in the presence of the target, binds to it, wherein the target-binding antibody is non-covalently bound to the labeling protein, wherein the labeling protein comprises a monovalent anti-Fc antibody fragment comprising an Fc binding region that non-covalently binds to the Fc region on the target-binding antibody, wherein the labeling protein is independently covalently linked to one or more labels at a region other than the Fc binding region, wherein the one or more labels may be the same or different;
    b) combining in the reaction vessel, the labeling mixture with a capture component to form a immunolabeling complex, wherein the capture component is capable of binding to labeling protein that did not bind to the target-binding antibody, and when unbound labeling protein is present, binds to the unbound labeling protein;
    c) removing the immunolabeling complex from the reaction vessel;
    d) combining the immunolabeling complex with the sample; and
    e) detecting the presence or absence of the label whereby the presence or absence of said target is determined.

2. The method according to claim 1, wherein the labeling mixture contains two or more distinct target-binding antibodies non-covalently bound by labeling proteins, wherein one of the target-binding antibodies is non-covalently bound by a first labeling protein and the other target-binding antibody is non-covalently bound by a second labeling protein.

3. The method according to claim 1, wherein the target-binding antibody has two or more different labeling proteins non-covalently bound to the antibody and at least one labeling protein is detectably distinct from other labeling proteins.

4. The method according to claim 1, wherein the anti-Fc antibody fragment is derived from a monoclonal antibody or polyclonal antibody.

5. The method according to claim 4, wherein the polyclonal antibody is a rabbit or a goat polyclonal antibody.

6. The method according to claim 4, wherein the monoclonal antibody is classified as mouse IgM, IgG1, IgG2a, IgG2b, or IgG3 antibody, or an equivalent thereof.

7. The method according to claim 1, wherein the label is selected from the group consisting of a fluorescent dye, a phosphorescent dye, a tandem dye, a particle, an electron transfer agent, biotin, a hapten, an enzyme and a radioisotope.

8. The method according to claim 7, wherein the fluorescent dye is selected from the group consisting of a xanthene, a cyanine, a coumarin and a phycobiliprotein.

9. The method according to claim 7, wherein the tandem dye is selected from the group consisting of cyanine-phycobiliprotein and xanthene-phycobiliprotein.

10. The method according to claim 1, wherein the biological sample comprises eukaryotic or prokaryotic cells, cellular extract, subcellular component, proteins, peptides, tissue culture, tissue, a bodily fluid, or a portion or combination thereof.

11. The method according to claim 10, wherein the sample is immobilized on a surface.

12. The method according to claim 10, wherein the sample is in a gel or on a blot or in an array.

13. The method according to claim 1, wherein the amount of target-binding antibody is about 5 micrograms to about 0.001 micrograms.

14. The method according to claim 1, wherein the capture component is an antibody or an antibody fragment, and is optionally attached to a microsphere or to agarose.

15. The method according to claim 14, wherein the labeling mixture contains at least one target-binding antibody non-covalently bound to a labeling protein and
    i) the labeling protein is a fragment of a rabbit or goat polyclonal antibody or of a mouse antibody,
    ii) the labeling protein is an anti-Fc antibody fragment that is a monovalent Fab or Fab' fragment, wherein the labeling protein is covalently labeled with one or more labels that are selected from the group consisting of a xanthene dye, a cyanine dye, a coumarin, a phycobiliprotein dye, cyanine-phycobiliprotein tandem dye, and xanthene-phycobiliprotein tandem dye, which labels are optionally the same or different; and the capture component is an antibody or an antibody fragment, which is optionally attached to a microsphere or to agarose.

16. A method for determining the presence of a first and second desired targets in a biological sample, said method comprising:
a) combining in a first reaction vessel, a first target-binding antibody comprising an Fc region with a first labeling protein to form a first labeling mixture, wherein the first-target binding antibody is capable of binding to the first target, and in the presence of the first target, binds to it, wherein the first target-binding antibody is non-covalently bound to a first labeling protein, and wherein the first labeling protein comprises a monovalent anti-Fc antibody fragment comprising an Fc binding region that non-covalently binds to the Fc region of the first target-binding antibody;
b) combining in a second reaction vessel, a second target-binding antibody comprising an Fc region with a second labeling protein to form a second labeling mixture, wherein the second targeting-binding antibody is capable of binding to the second target, and in the presence of the second target, binds to it, wherein the second target-binding antibody is non-covalently bound to the second labeling protein, and wherein the second labeling protein comprises a monovalent anti-Fc antibody-fragment comprising an Fc binding region that non-covalently binds to the Fc region of the second target-binding antibody;
c) combining in the first reaction vessel, the first labeling mixture with a first capture component to form a first immunolabeling complex, wherein the first capture component is capable of binding to the first labeling protein that did not bind to the first target-binding antibody, and when unbound first labeling protein is present, binds to the unbound first labeling protein;
d) combining in the second reaction vessel, the second labeling mixture with a second capture component to form a second immunolabeling complex, wherein the second capture component is capable of binding to the second labeling protein that did not bind to the second target-binding antibody, and when unbound second labeling protein is present, binds to the unbound second labeling protein;
e) removing the first immunolabeling complex from the first reaction vessel;
f) removing the second immunolabeling complex from the second reaction vessel;
g) combining the first and second immunolabeling complexes with the sample; and
h) detecting the presence or absence of said labels whereby the presence or absence of said target is determined;
wherein the monovalent anti-Fc antibody fragments are detectably distinct, and wherein the labeling proteins are covalently linked to one or more labels at a region other than the Fc binding region.

17. The method according to claim 16, wherein the first and second antibody fragments are derived from a monoclonal antibody or polyclonal antibody.

18. The method according to claim 17, wherein the polyclonal antibody is a rabbit or a goat polyclonal antibody.

19. The method according to claim 17, wherein the monoclonal antibody is classified as mouse IgM, IgG1, IgG2a, IgG2b, or IgG3 antibody, or an equivalent thereof.

20. The method according to claim 16, wherein the labels are selected from the group consisting of a fluorescent dye, a phosphorescent dye, a tandem dye, a particle, an electron transfer agent, biotin, a hapten, an enzyme and a radioisotope.

21. The method according to claim 20, wherein the fluorescent dye is selected from the group consisting of a xanthene dye, a cyanine dye, a coumarin dye, and a phycobiliprotein dye.

22. The method according to claim 20, wherein the tandem dye is selected from the group consisting of cyanine-phycobiliprotein and xanthene-phycobiliprotein.

23. The method according to claim 16, wherein the biological sample comprises eukaryotic or prokaryotic cells, cellular extract, subcellular component, tissue culture, tissue, a bodily fluid, or a portion or combination thereof.

24. The method according to claim 23, wherein the amount of target-binding antibody is about 5 micrograms to about 0.001 micrograms.

25. The method of claim 16, wherein the sample is immobilized on a solid surface.

26. The method of claim 16, wherein the sample is in a gel, or on a blot or in an array.

27. The method according to claim 16, wherein the capture component is an antibody or an antibody fragment, and is optionally attached to a microsphere or to agarose.

28. The method according to claim 16, wherein the labeling mixture contains at least two target-binding antibodies each bound by at least one labeling protein; and
a) the first and second labeling proteins are independently a fragment of a rabbit or goat polyclonal antibody or a mouse antibody,
b) the first and second labeling proteins are an anti-Fc antibody fragment that is a monovalent Fab or Fab' fragment, wherein the first and second labeling proteins are covalently labeled with one or more labels that are independently selected from the group consisting of a xanthene dye, a cyanine dye, a coumarin, a phycobiliprotein dye, a cyanine-phycobiliprotein tandem dye, and xanthene-phycobiliprotein tandem dye, which labels are optionally the same or different; and the capture component is an antibody or an antibody fragment, which is optionally attached to a microsphere or to agarose.

29. A method according to claim 1, further comprising stabilizing binding of the target-binding antibody to said labeling protein.

30. The method according to claim 7, wherein the enzyme is selected from the group consisting of peroxidase, phosphatase, glycosidase, and luciferases.

31. The method according to claim 30, wherein the method further comprises adding an enzymatic substrate selected from the group consisting of a chromogenic, fluorogenic and chemiluminescent substrate.

32. The method according to claim 20, wherein the enzyme is selected from the group consisting of peroxidase, phosphatase, glycosidase, and luciferases.

33. The method according to claim 32, wherein the method further comprises adding an enzymatic substrate selected from the group consisting of a chromogenic, fluorogenic and chemiluminescent substrate.

* * * * *

UNITED STATES PATENT AND TRADEMARK OFFICE
CERTIFICATE OF CORRECTION

| | | |
|---|---|---|
| PATENT NO. | : 8,323,903 B2 | Page 1 of 1 |
| APPLICATION NO. | : 10/118204 | |
| DATED | : December 4, 2012 | |
| INVENTOR(S) | : Archer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 224 days.

Signed and Sealed this
Second Day of December, 2014

Michelle K. Lee
*Deputy Director of the United States Patent and Trademark Office*